United States Patent [19]
Lees et al.

[11] Patent Number: 5,955,055
[45] Date of Patent: Sep. 21, 1999

[54] SYNTHETIC PEPTIDES FOR ARTERIAL IMAGING AT VASCULAR IMAGING SITES

[75] Inventors: Robert S. Lees; Ann M. Lees, both of Brookline; Allan Fischman, Boston, all of Mass.; Ing-Lung Shih, Taiwan, Taiwan; Mark A. Findeis, Boston, Mass.

[73] Assignee: New England Deaconess Hospital Corporation, Boston, Mass.

[21] Appl. No.: 08/469,692

[22] Filed: Jun. 6, 1995

Related U.S. Application Data

[62] Division of application No. 08/398,046, Feb. 28, 1995, which is a continuation of application No. 08/201,057, Feb. 24, 1994, abandoned, which is a continuation of application No. 08/048,569, Apr. 16, 1993, abandoned, which is a continuation of application No. 07/694,929, May 2, 1991, abandoned, which is a continuation-in-part of application No. 07/518,215, May 3, 1990, abandoned, which is a continuation-in-part of application No. 07/518,142, May 3, 1990, abandoned, which is a continuation-in-part of application No. 07/189,130, May 2, 1988, abandoned.

[51] Int. Cl.[6] ............................................. A61K 51/08
[52] U.S. Cl. ..................... 424/1.69; 530/301; 530/324; 530/326
[58] Field of Search ........................... 424/1.69; 530/301, 530/324, 326

[56] References Cited

U.S. PATENT DOCUMENTS

| | | | |
|---|---|---|---|
| 4,116,776 | 9/1978 | Dalbow et al. | 195/103.7 |
| 4,359,453 | 11/1982 | Gordon | 424/1 |
| 4,577,636 | 3/1986 | Spears | 128/654 |
| 4,643,988 | 2/1987 | Segrest et al. | 514/12 |
| 4,647,445 | 3/1987 | Lees | 424/1.1 |
| 4,660,563 | 4/1987 | Lees | 128/654 |
| 4,668,503 | 5/1987 | Hnatowich | 424/1.1 |
| 4,937,067 | 6/1990 | Lees | 424/1.1 |
| 5,096,696 | 3/1992 | Galankis | 424/1.1 |
| 5,217,705 | 6/1993 | Reno et al. | 424/1.1 |
| 5,380,646 | 1/1995 | Knight et al. | 424/1.69 |
| 5,395,609 | 3/1995 | Stuttle | 424/1.69 |
| 5,455,158 | 10/1995 | Vogel et al. | 435/7.21 |
| 5,556,609 | 9/1996 | Zamora | 424/1.69 |

FOREIGN PATENT DOCUMENTS

| | | |
|---|---|---|
| 0135125 | 3/1985 | European Pat. Off. . |
| 0137457 | 4/1985 | European Pat. Off. . |
| 0163041 | 12/1985 | European Pat. Off. . |
| 0189688 | 8/1986 | European Pat. Off. . |
| WO 85/04329 | 10/1985 | WIPO . |
| WO 91/16919 | 11/1991 | WIPO . |

OTHER PUBLICATIONS

Urry et al., "pK Shift of Functional Group in Mechanochemical Coupling Due to Hydrophobic Effect: Evidence for an apolar–polar repulsion free energy in water", 1988, Bichem. and Biophys. Research Commun., 153(2):832–39.

Cardin et al., 1982, Biochemistry, 21:4503, Sulfhydryl Chemistry and Solubility Properties of Human Plasma Apolipoprotein B.

Lees and Myers, 1982, Advances in Internal Medicine, 27:475, Noninvasive Diagnosis of Arterial Disease.

Camejo, 1982, Advances in Lipid Research, 19:1, The Interaction of Lipids and Lipoproteins with the Intercellular Matrix of Arterial Tissue: Its Possible Role in Atherogenesis.

(List continued on next page.)

Primary Examiner—Gary E. Hollinden
Attorney, Agent, or Firm—Clark & Elbing LLP

[57] ABSTRACT

Vascular disease including asymptomatic atherosclerosis can be diagnosed by administering a synthetic peptide or peptide analog having an affinity for, and propensity to accumulate at, a site of vascular injury to a patient, and then detecting the location of the peptide or peptide analog within the patient's vascular system. The synthetic peptide or peptide analog may include an amino acid sequence sufficiently duplicative of the amino acid sequence of a region of either the apolipoprotein B, apolipoprotein A-I, or elastin proteins such that the peptide or peptide analog accumulates at a site of vascular injury.

20 Claims, 12 Drawing Sheets

OTHER PUBLICATIONS

Camejo et al., 1983, Artherosclerosis 49:241, Partial Structure of the Active Moiety of a Lipoprotein Complexing Proteoglycan from Human Aorta.

Lees and Lees, 1983, Proc. Natl. Acad. Sci. USA, 80:5098, Low Density Lipoprotein Degradation by Mononuclear Cells from Normal and Dyslipoproteinemic Subjects.

Roberts et al., 1983, Journal of Lipid Research, 24:1160, Selective Accumulation of Low Density Lipoproteins in Damaged Arterial Wall.

Lees et al., 1983, J. Nucl. Med. 24:154, External Imaging of Human Atherosclerosis.

Hnatowich et al., 1983, Science 220:613, Radioactive Labeling of Antibody: A Simple and Efficient Method.

Mateu et al., 1984, Biochemica et Biophysica Acta, 795:525, The Structural Stability of Low–Density Lipoprotein. A Kinetic X–Ray Scattering Study of its Interaction with Arterial Proteoglycans.

Meares et al., 1984, Analytic Biochemistry, 142:68, Conjugation of Antibodies with Bifunctional Chelating Agents: Isothiocyanate and Bromoacetamide Reagents, Methods of Analysis, and Subsequent Addition . . . .

Stewart et al., 1984, Solid Phase Peptide Synthesis. Laboratory Techniques in Peptide Synthesis, pp. 53–63.

Carlsson et al., 1985, Nucleic Acids Research, 13:8813, Molecular Cloning of Human Apolipoprotein B CDNA.

Forgez et al., 1986, Biochemical and Biophysical Research Communications, 140:250, Identification of Surface Exposed Segments of Apolipoprotein B–100 in the LDL Particle.

Knott et al., 1986, Nature, 323:734, Complete Protein Sequence and Identification of Structural Domains of Human Apolipoprotein B.

Law et al., 1986, Proc. Natl. Acad. Sci. USA, 83:8142, Human Liver Apolipoprotein B–100 CDNA: Complete Nucleic Acid and Derived Amino Acid Sequence.

Wegrowski et al., 1986, Biochem. J., 235:823, Proteoglycans from Pig Aorta.

Yang et al., 1986, Nature, 323:738, Sequence, Structure, Receptor–Binding Domains and Internal Repeats of Human Apolipoprotein B–100.

Fischman et al., 1987, Arteriosclerosis, 7:361, Accumulation of Native and Methylated Low Density Lipoproteins by Healing Rabbit Arterial Wall.

Lusis et al., 1985, Proc. Natl. Acad. Sci. USA, 82:4597, Cloning and Expression of Apolipoprotein B, the Major Protein of Low and Very Low Density Lipoproteins.

Hollander et al., 1979, Arthrosclerosis, 34:391, Soluble Proteins in the Human Atherosclerotic Plaque.

Blood et al., 1988, J. Cell Biology, 107:1987, Identification of a Tumor cell Receptor for VGVAPG, an Elastin–Derived Chemotactic Peptide.

Schultz et al., 1979, Principles of Protein Structure, published by Springer–Verlag (N.Y.).

Van Vunakis et al., 1980, Methods in Enzymology, 70:201, Immunochemical Techniques Part A.

Shih et al., 1990, Proc. Natl. Acad. Sci., 87:1436, Focal Accumulation of an Apolipoprotein B–Based Synthetic Oligopeptide in the Healing Rabbit Arterial Wall.

Baule et al., 1988, Biochem. Biophys. Res. Comm., 154:1054, Multiple Chick Tropoelastin MRNAS.

Senior et al., 1984, Journal of Cell Biology, 99:870, VAL–GLY–VAL–ALA–PRO–GLY–, A Repeating Peptide in Elastin, is Chemotactic for Fibroblasts and Monocytes.

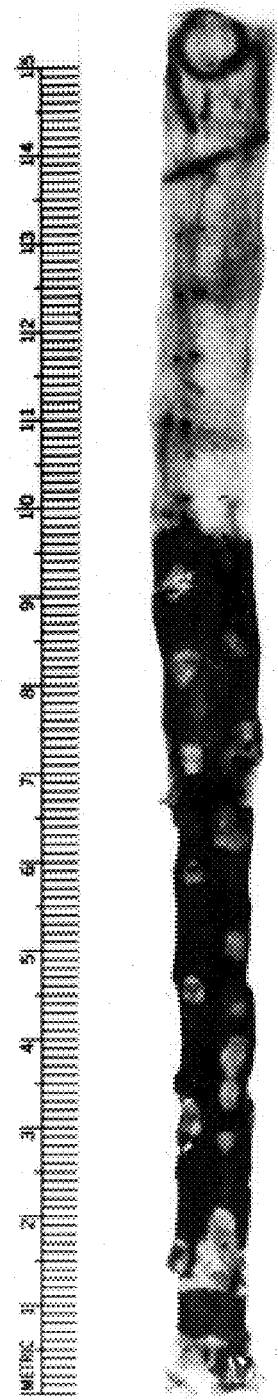 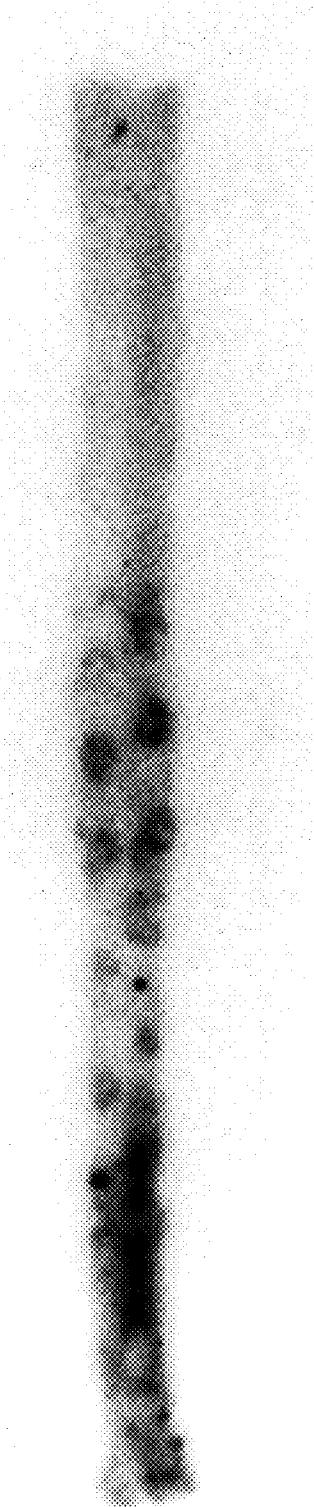
Fig. 9A
Fig. 9B

SYNTHETIC PEPTIDES FOR ARTERIAL IMAGING AT VASCULAR IMAGING SITES This is a divisional of copending application Ser. No. 08/398,046 filed on Feb. 28, 1995, which in turn is a continuation of Ser. No. 08/201,057 filed on Feb. 24, 1994, now abandoned, which in turn is a continuation of Ser. No. 08/048,569 filed Apr. 16, 1993, now abandoned, which in turn is a continuation of Ser. No. 07/694,929 filed May 2, 1991, now abandoned, which in turn is a continuation-in-part of Ser. No. 07/518,215 filed May 3, 1990, now abandoned, which in turn is a continuation-in-part of Ser. No. 07/518,142 filed on May 3, 1990, now abandoned, which in turn is a continuation-in-part of Ser. No. 07/189,130 filed on May 2, 1988, now abandoned.

The U.S. Government has rights in this invention pursuant to NIH Grant No. HL32975.

BACKGROUND OF THE INVENTION

The invention relates to methods and means useful for the early detection of vascular disease, such as atherosclerosis, particularly, methods and means employing labelled synthetic peptides to detect arterial injury.

Atherosclerosis is a disease which causes the thickening and hardening of the arteries, particularly the larger artery walls. It is characterized by lesions or raised fibrous plaques which form within the arterial lumen. The plaques are most prevalent in the abdominal aorta, coronary arteries, or carotid arteries, and they increase progressively with age. They commonly present dome-shaped, opaque, glistening surfaces which distort the lumen. A lesion typically will consist of a central core of lipid and necrotic cell debris, capped by a collagen fibromuscular layer. Complicated lesions will also include calcified deposits and exhibit various degrees of necrosis, thrombosis, and ulceration.

The injury at, or deformities of, the arterial lumen presented by the plaque and associated deposits result in occluded blood flow, and ultimately in angina, cerebral ischemia, renal hypertension, ischemic heart disease, stroke, and diseases of other organs, if untreated. At present, coronary atherosclerosis is still the leading cause of death in the United States, claiming the lives of over a half million Americans annually, roughly twice as many as are killed by cancer.

Unfortunately, there are no existing diagnostic methods which can detect the early stages of atherosclerosis and related vascular diseases which often are clinically silent. Since lifestyle changes, drug therapy, and other means exist for delaying or reducing vascular occlusion or the stresses on various body organs which result from atherosclerotic lesions, the early detection of atheromatous plaques in the vascular system would be of considerable value in permitting preventive intervention at a time when it can be most effective.

Arteriography, the conventional approach to diagnosing vascular disease, involves catheterization and the injection of radiopaque substances into the bloodstream in order to image obstructions in the arteries. This procedure involves significant morbidity, in that infection, perforation of the artery, arrhythmia, stroke, infarction, and even death can occur. Because of the risks involved, arteriograms typically are reserved for individuals with advanced or acute atherosclerotic disease.

A variety of less invasive techniques for the diagnosis of vascular injury and disease have been proposed. These techniques include plethysmography, thermography, and ultrasonic scanning (Lees and Myers, *Adv. Int. Med.* 27:475, 1982).

Other non-invasive approaches to the diagnosis of vascular injury which have been proposed by the present inventor involve the administration of labelled target-seeking biologically active molecules or antibodies which preferentially seek out arterial lesions (U.S. patent application Ser. No. 929, 012, entitled "Detection of Vascular Disease", filed Nov. 10, 1986) and the administration of labelled low density lipoproteins (LDLS) to the vascular system of a patient (U.S. Pat. Nos. 4,647,445 and 4,660, 563). LDLs circulating in the blood are known to bind to atherosclerotic plaques (Lees et al., *J. Nucl. Med.* 24:154, 1983). This binding most likely occurs via apolipoprotein B-100 (apo B-100), the protein moiety of the LDL molecule, which is responsible for the removal of LDL from the circulation by receptor-mediated uptake in a variety of cell types. LDLs conjugated to a radioactive label can be used to provide information on the location and extent of plaque in the vascular system by imaging them with a radiation detector. Alternatively, LDLs can be labelled with a non-radioactive, paramagnetic contrast agent capable of detection in magnetic resonance imaging (MRI) systems.

One disadvantage to this method is that several days are typically required to isolate LDLs from the patient's blood and to label them. Often, such a delay in diagnosis and subsequent treatment is detrimental for critically ill patients. Further, an additional risk of viral infection is incurred if donor blood is employed as an LDL source.

Consequently, there exists a need for better noninvasive techniques and reagents capable of detecting and mapping early, non-stenosing, non-flow-disturbing atherosclerotic arterial lesions.

Accordingly, it is an object of the present invention to provide synthetic peptides which are useful for detecting and imaging vascular disease or injury.

It is another object of the invention to provide synthetic peptides useful for imaging which are inexpensive and easy to prepare.

It is yet another object of the invention to provide an improved method of detecting and mapping vascular injury, including vascular injury at its early stages.

Yet another object of the present invention is to provide a method, which is non-invasive, of detecting and mapping vascular injury.

Finally, it is an object of the present invention to provide synthetic peptides for the prevention or treatment of vascular damage.

SUMMARY OF THE INVENTION

In general, the invention features a peptide or peptide analog having an affinity for, and propensity to accumulate at, a site of vascular injury.

By "peptide" is meant any chain of 30 amino acids or less. By "peptide analog" is meant a peptide which differs in amino acid sequence from the native peptide only by conservative amino acid substitutions, for example, substitution of Leu for Val, or Arg for Lys, etc., or by one or more non-conservative amino acid substitutions, deletions, or insertions located at positions which do not destroy the biological activity of the peptide (in this case, the ability of the peptide to target vascular lesions). A peptide analog, as used herein, may also include, as part or all of its sequence, one or more amino acid analogues, molecules which mimic the structure of amino acids, and/or natural amino acids found in molecules other than peptide or peptide analogues.

In preferred embodiments, the peptide or peptide analog is water soluble; or is soluble in a physiological fluid, preferably, one which is at physiological pH, for example, blood plasma.

In another preferred embodiment, the peptide has a molecular conformation analogous to the molecular conformation (size, shape, charge) of a surface region of the apolipoprotein B (apo B) moiety of LDL. Alternatively, the peptide or peptide analog may have an amino acid sequence sufficiently duplicative of at least a portion of a surface region of the apolipoprotein B moiety of LDL, such that the peptide or peptide analog accumulates at a site of vascular injury in a manner characteristic of LDL. Such a surface region is preferably amphiphilic (i.e., having both a hydrophobic and a hydrophilic surface) and is, preferably, also α-helical. Examples of preferred peptide or peptide analogues include:

Tyr-Arg-Ala-Leu-Val-Asp-Thr-Leu-Lys-Phe-Val-Thr-Gln-Ala-Glu-Gly-Ala-Lys; (SEQ ID NO:1)

Tyr-Lys-Leu-Ala-Leu-Glu-Ala-Ala-Arg-Leu-Leu-Ala-Asp-Ala-Glu-Gly-Ala-Lys; (SEQ ID NO:2)

Tyr-Lys-Leu-Ala-Leu-GlU-Ala-Ala-Arg-Leu-Leu-Ala-Asn-Ala-Glu-Gly-Ala-Lys; SEQ ID NO:3

Tyr-Arg-Ala-Leu-Val-Asp-Tyr-Leu-Lys-Phe-Val-Thr-Gln-Leu; SEQ ID NO:4

Tyr-Arg-Ala-Leu-Val-Asp-Thr-Leu-Lys; SEQ ID NO:5

Tyr-Ala-Lys-Phe-Arg-Glu-Thr-Leu-Glu-Asp-Thr-Arg-Asp-Arg-Met-Tyr; SEQ ID NO:6

Tyr-Ala-Ala-Leu-Asp-Leu-Asn-Ala-Val-Ala-Asn-Lys-Ile-Ala-Asp-Phe-Glu-Leu; SEQ ID NO:7

Tyr-Arg-Ala-Leu-Val-Asp-Thr-Leu-Lys-Phe-Val-Thr-Glu-Gln-Ala-Lys-Gly-Ala; and SEQ ID NO:8

Tyr-Arg-Ala-Leu-Val-Asp-Thr-Glu-Phe-Lys-Val-Lys-Gln-GluAla-Gly-Ala-Lys SEQ ID NO:9.

In another preferred embodiment, the peptide or peptide analog includes an amphiphilic domain, preferably including an α-helix, and has a net charge of −2 or greater, such that the peptide or peptide analog accumulates at a site of vascular injury. In various preferred embodiments, the peptide or peptide analog is derived from a vascular-associated protein. Preferably, the vascular-associated protein is apolipoprotein A-I (apoA-I) or, more preferably, apolipoprotein B.

By "net charge" is meant the total charge on a peptide at neutral pH and is calculated by adding together the charge (at neutral pH) on each of the amino acids of the peptide. By "derived from" is meant having an amino acid sequence identical or substantially identical to the sequence of, as used herein, a vascular-associated protein. By "substantially identical to" is meant having an amino acid sequence which differs only by conservative amino acid substitutions (as described above) or by non-conservative amino acid substitutions, deletions, or insertions located at positions which do not destroy the biological activity of the peptide (also as described above). By a "vascular-associated protein" is meant a protein that is naturally associated either with the vascular wall or with an extracellular component of the vascular system, including the proteins elastin and collagen, and carbohydrates such as proteoglycans.

In other preferred embodiments, the peptide or peptide analog has a net charge of −2 or greater and has an amino acid sequence sufficiently duplicative of that of at least a portion of an amphiphilic domain of apolipoprotein A-I such that the peptide or peptide analog accumulates at sites of vascular injury. A preferred peptide or peptide analog is:

Tyr-Val-Leu-Asp-Glu-Phe-Arg-Glu-Lys-Leu-Asn-Glu-Glu-Leu-Glu-Ala-Leu-Lys-Gln-Lys SEQ ID NO: 10.

In yet another preferred embodiment, the peptide or peptide analog includes a hydrophobic domain and has a net charge of −2 or greater, such that the peptide or peptide analog accumulates at the site of vascular injury. Preferably, the peptide or peptide analog is derived from a vascular-associated protein, for example, elastin; the peptide or peptide analog has an affinity for a vascular wall component, for example, a collagen, a proteoglycan, or elastin; the peptide or peptide analog binds elastin with a dissociation constant of $10^{-6}$ or less (i.e., or with greater affinity, as measured in vitro by the method of Podet et al., *Arteriosclerosis and Thrombosis* 11:116, 1991); the hydrophobic domain of the peptide or peptide analog includes a β-strand. In other preferred embodiments, the vascular-associated protein is a peptide or peptide analog having a net charge of −2 or greater and an amino acid sequence sufficiently duplicative of that of at least a portion of elastin such that the peptide or peptide analog accumulates at sites of vascular injury. A preferred peptide or peptide analog may include the amino acid sequence:

Tyr-(Val-Gly-Val-Ala-Pro-Gly)$_x$ (SEQ ID NO: 11), wherein x is at least 1 and, preferably, 3 (SEQ ID NO:14); or the peptide or peptide analog may include the amino acid sequence:

Tyr-(Val-Pro-Gly-Val-Gly)$_x$ (SEQ ID NO:12), wherein x is at least 1 and, preferably, 3 or, (SEQ ID NO 11)more preferably, 4 (SEQ ID NO:13).

In various other preferred embodiments, the peptide or peptide analog has an acetylated amino terminus and/or an amidated carboxy terminus. Examples of such peptide or peptide analogues include:

NH$_2$-Tyr-Arg-Ala-Leu-Val-Asp-Thr-Leu-LYs-Phe-Val-Thr-Gln-Ala-Glu-Gly-Ala-Lys-CONH$_2$ (SEQ ID NO:1);

CH$_3$CONH-Tyr-Arg-Ala-Leu-Val-Asp-Thr-Leu-Lys-Phe-Val-Thr-Gln-Ala-Glu-Gly-Ala-Lys-CONH$_2$ SEQ ID NO:1;

H$_2$N-Tyr-Lys-Leu-Ala-Leu-Glu-Ala-Ala-Arg-Leu-Leu-Ala-Asp-Ala-Glu-Gly-Ala-Lys-CONH$_2$ SEQ ID NO:2;

CH$_3$CONH-Tyr-Lys-Leu-Ala-Leu-Glu-Ala-Ala-Arg-Leu-Leu-Ala-Asp-Ala-Glu-Gly-Ala-Lys-CONH$_2$ SEQ ID NO:2;

H$_2$N-Tyr-Lys-Leu-Ala-Leu-Glu-Ala-Ala-Arq-Leu-Leu-Ala-Asn-Ala-Glu-Gly-Ala-Lys-CONH$_2$ SEQ ID NO:3;

CH$_3$CONH-Tyr-Lys-Leu-Ala-Leu-Glu-Ala-Ala-Arg-Leu-Leu-Ala-Asn-Ala-Glu-Gly-Ala-Lys-CONH$_2$ SEQ ID NO:3

CH$_3$CONH-Tyr-Arg-Ala-Leu-Val-Asp-Tyr-Leu-Lys-Phe-Val-Thr-Gln-Leu-CONH$_2$ SEQ ID NO:3;

CH$_3$CONH-Tyr-Arg-Ala-Leu-Val-Asp-Thr-Leu-Lys-CONH$_2$ SEQ ID NO:5;

CH$_3$CONH-Tyr-Ala-Lys-Phe-Arg-Glu-Thr-Leu-Glu-Asp-Thr-Arg-Asp-Arg-Met-Tyr-CONH$_2$ SEQ ID NO:6;

H$_2$N-Tyr-Ala-Ala-Leu-Asp-Leu-Asn-Ala-Val-Ala-Asn-Lys-Ile-Ala-Asp-Phe-Glu-Leu-CONH$_2$ SEQ ID NO:7;

CH$_3$CONH-Tyr-Arg-Ala-Leu-Val-Asp-Thr-Leu-Lys-Phe-Val-Thr-Glu-Gln-Ala-Lys-Gly-Ala-CONH$_2$ SEQ ID NO:8;

CH$_3$CONH-Tyr-Arg-Ala-Leu-Val-Asp-Thr-Glu-Phe-Lys-Val-Lys-Gln-Glu-Ala-Gly-Ala-Lys-CONH$_2$ SEQ ID NO:9;

CH$_3$CONH-Tyr-Val-Leu-Asp-GlU-Phe-Arg-Glu-LYs-Leu-Asn-Glu-Glu-Leu-Glu-Ala-Leu-Lys-Gln-Lys-CONH$_2$ SEQ ID NO:10;

H$_2$N-Tyr-Val-Pro-Gly-Val-Gly-Val-Pro-Gly-Val-Gly-Val-Pro-Gly-Val-Gly-Val-Pro-Gly-Val-Gly-CONH$_2$; SEQ ID NO:13 and H$_2$N-Tyr-Val-Gly-Val-Ala-Pro-Gly-Val-Gly-Val-Ala-Pro-Gly-Val-Gly-Val-Ala-Pro-Gly-CONH$_2$ SEQ ID NO:14.

The synthetic peptide or peptide analogues are useful for detecting and imaging injury in the vascular system of a subject. Other useful synthetic peptide or peptide analogues may include: amino acid analogues, molecules which mimic the structure of amino acids, and natural amino acids found in molecules other than peptide or peptide analogues.

In other preferred embodiments, the peptide or peptide analog may be linked to a detectable label to enable its monitoring within the subject. Preferable labels include a radioisotope, e.g., $^{131}$I, $^{125}$I, $^{123}$I, $^{111}$In, $^{99m}$Tc, $^{203}$Pb, $^{198}$Hg, Ru$^{97}$, or $^{201}$Tl; or a paramagnetic contrast agent. Such labels may enable the extracorporeal monitoring of synthetic peptide or peptide analogues within the vascular system of the subject with, for example, a gamma scintillation camera or an MRI system.

In another aspect, the invention features a method for the detection of injury (for example, atherosclerosis) in the vascular system of a subject involving introducing into a subject a peptide or peptide analog of the forms set forth above. The method may further involve administering a second peptide or peptide analog of the forms set forth above. The peptide or peptide analog to be introduced may be administrated by arterial or venous injection. Alternatively, a non-hydrolyzable derivative may be administered orally or nasally. The introduced synthetic peptide or peptide analog is then allowed to circulate within the vascular system of the subject, whereby at least a portion of it accumulates at a site of injury. The portion of the synthetic peptide or peptide analog which has accumulated at a site of injury is then detected. The detection step may further include quantitating the amount of labelled peptide or peptide analog which has accumulated at a site of vascular injury; or imaging the region of the subject's vascular system at which the synthetic peptide or peptide analog has accumulated, e.g., by extracorporeal monitoring of a peptide or peptide analog having a detectable label (e.g., a radioactive label or a paramagnetic contrast agent) with a gamma scintillation camera or a magnetic resonance imaging system.

In a final aspect, the invention includes a method for inhibiting the binding of low density lipoprotein to the vascular wall(s) of a subject involving administering to the subject a therapeutically-effective amount of a peptide or peptide analog of the forms set forth above.

Applicants have discovered that vascular diseases, including asymptomatic atherosclerosis, can be diagnosed by administering a synthetic peptide to a subject, and then detecting the location, pattern, and concentration of the peptide following its accumulation at sites of injury within the subject's vascular system. The technique affords a number of advantages. It is non-invasive; it requires neither complex medical equipment, nor highly skilled medical practitioners to be successfully accomplished; and the peptides used to target vascular lesions may be produced inexpensively, quickly, and in large quantity (e.g., by recombinant DNA technology).

In addition, the peptides of the invention may be used for the prevention or alleviation of vascular diseases such as atherosclerosis. Administration of the peptides of the invention in therapeutically-effective doses can prevent the accumulation of LDL by blocking LDL binding sites.

Other features and advantages of the invention will be apparent from the following description of the preferred embodiments, and from the claims.

BRIEF DESCRIPTION OF THE DRAWINGS

The foregoing and other objects of the invention, the various features thereof, as well as the invention itself, may be more fully understood from the following description when read together with the accompanying drawings in which:

FIG. 9 shows a photograph (A) and an onlay autoradiograph (B) of the abdominal aorta of a rabbit treated with 125I-labelled synthetic peptide, SP-19a;

FIG. 10 shows a photograph (A) and an onlay autoradiograph (B) of the abdominal aorta of a rabbit treated with $^{125}$I-labelled synthetic peptide, SP-21a;

DETAILED DESCRIPTION

Figure 1:
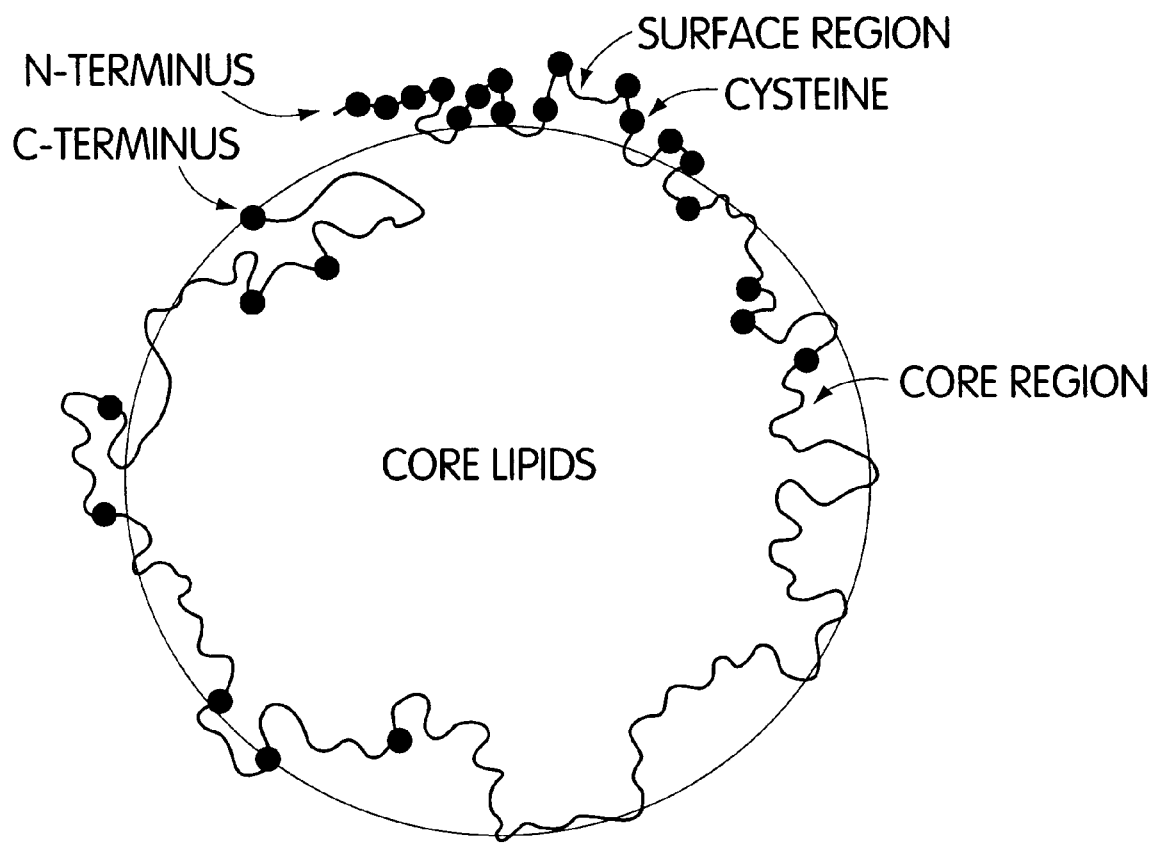
FIG. 1 shows a schematic model of the apo B-100 configuration, when included in the LDL molecule, and surface-exposed regions.
Figure 2A:
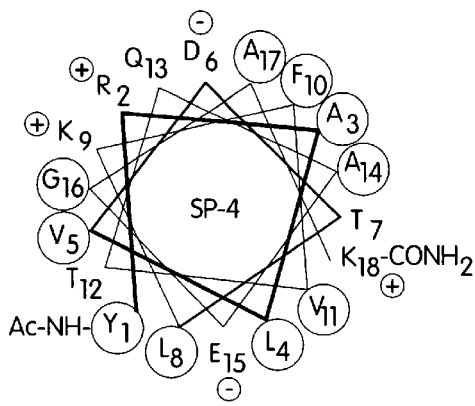
FIG. 2 is a series of helical wheel diagrams indicating the amphiphilic character of representative synthetic peptides.
Figure 2B:
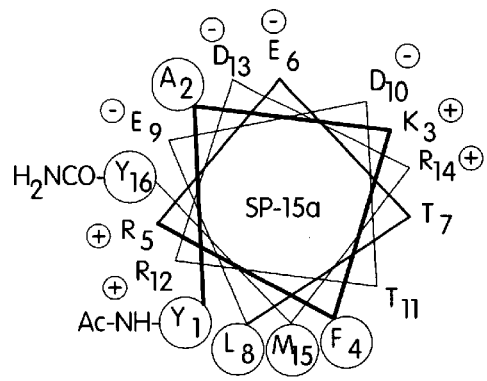
Figure 2C:
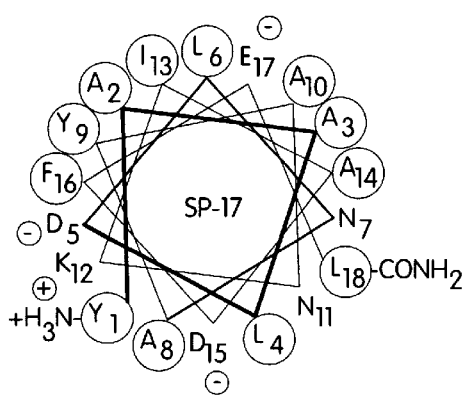
Figure 2D:
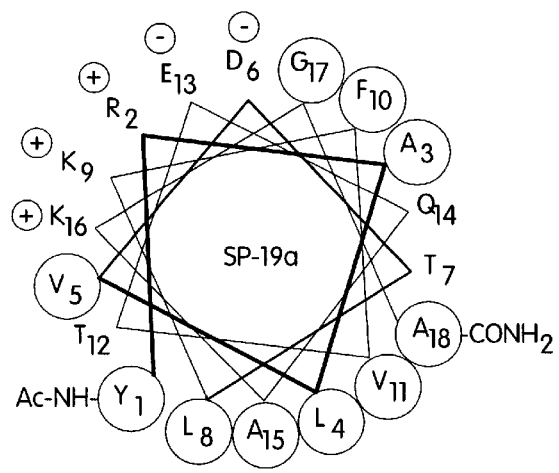
Figure 2E:
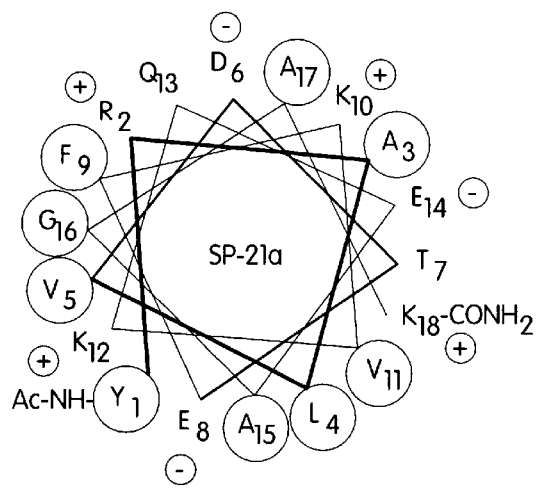
Figure 2F:
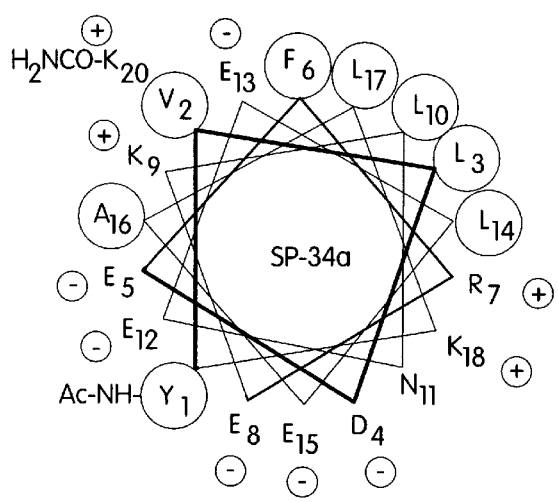

This invention provides synthetic peptides which have affinity for, and the propensity to accumulate at, a site of vascular injury, and therefore are useful in detecting, diagnosing, monitoring, and treating vascular disease.

Specific examples of such synthetic peptides having these characteristics may have an amino acid sequence that is analogous to portions of known polypeptides which have an affinity for a site of vascular injury, i.e., have a molecular conformation, charge, and/or size which is similar to that part of the polypeptide (e.g., low density lipoprotein or elastin) which is responsible for its affinity for arterial lesions. Alternatively, the synthetic peptides of the present invention may be homologous with portions of the apo B-100 moiety of LDL, the apo A-I moiety of HDL, or elastin.

Design and Synthesis of Peptides

Peptides useful in the invention are those which successfully target vascular lesions. Thus, it is preferable to fashion such peptides after the sequence of a protein which is "vascular-associated", i.e., naturally associated with a vascular cell surface or with an extracellular component of the vascular system (e.g., proteoglycans, collagen, or elastin). Proteins of this class include: apolipoprotein B (i.e., the protein moiety of low density lipoprotein) and elastin (a natural component of the arterial wall). It is not necessary, and it is often inconvenient, to use the entire protein molecule (see above). Applicants have discovered that protein fragments can also be used to effectively target vascular lesions. Examples of useful fragments are described herein. Applicants have shown that such fragments are of low net charge (i.e., between −2 and +2), allowing an interaction, e.g., with the highly negatively-charged vascular wall. Applicants have also shown that such peptides fall generally into one of two classes: (1) peptides which include an amphiphilic domain, preferably of a-helical character; and (2) peptides which include a hydrophobic domain (which facilitates interaction with a vascular surface or vascular-associated extracellular component) and a hydrophilic domain of either positive charge or low negative charge (i.e., −2 or greater; i.e., or more positive) which facilitates solubility.

Preferred peptides of class I, i.e., those peptides which include an amphiphilic domain (i.e., a domain which has both a hydrophobic and a hydrophilic surface) are identified, e.g., as described in Kaiser and Kezdy (*Ann. Rev. Biophys. Biophys. Chem.* 16: 561, 1987; *Science* 223:249, 1984). Typically, the amphiphilic domain includes a region of secondary structure, most commonly, an α-helix or a β-strand. Because α-helix-containing peptides are generally more soluble than β-strand-containing peptides, they are preferred in the invention; increased solubility facilitates in vitro peptide synthesis and peptide administration to a patient.

Preferred peptides of class II, i.e., those peptides which include both (a) a hydrophobic domain which facilitates interaction with a vascular cell surface or a hydrophobic vascular-associated component (e.g., elastin) and (b) a positively-charged or slightly negatively-charged domain that facilitates solubility are identified using e.g., the methods for predicting hydrophobicity and hydrophilicity described below. Applicants have shown that peptides of this class, even peptides including one or more domains predicted to form β-strands, may be administered to a subject and used to efficiently target arterial lesions. Peptides of this class likely interact with hydrophobic vascular-associated extracellular components.

The net charge of a peptide is calculated by adding together the charges on the amino acids of the peptide at neutral pH. The local charged character (i.e., amphiphilic, hydrophilic, or hydrophobic nature, e.g., of a region of a peptide) and secondary structure (i.e., the presence of an α-helix or α-strand) of a particular sequence of amino acids may be predicted from its primary sequence using any of a number of model-building approaches. For example, to identify an amphiphilic α-helix, one may construct an "Edmundson wheel", and look for the presence of hydrophobic and hydrophilic residues on opposite faces of the resultant cylinder (Schiffer and Edmundson, *Biophys. J.* 7:121, 1967; hereby incorporated by reference). Alternatively, to identify an amphiphilic, hydrophobic, or hydrophilic domain or a region of secondary structure, one may use a semi-empirical formula such as the Chou-Fasman method (Chou and Fasman, *Ann. Rev. Biochem.* 47:251, 1978; hereby incorporated by reference); or the program, PREDICT (based on the GOR method of secondary structure prediction) (Robson et al., Introduction to Proteins and Protein Engineering; Elsevier, New York, 1986; hereby incorporated by reference). Such a program makes use of the equation:

$$I_j(X) = \sum_{m=j-8}^{m=j+8} I(S_j = X : \overline{X}; R_{j+m})$$

where $I(S_j=X:X;R_{j+m})$ values are derived from a statistical preference for a residue j to be in a conformation X. The state of j is evaluated from a summation over m residues of sequence on either side of j; parameter values are dependent on the identity of the residue at each position and its contribution to each of the four structural types. Values are calculated for each of the states H, E, T, and C; the highest value determines the predicted structure (either H=α-helix, E=β-sheet, T=turn, or C=random coil). Finally, amphiphilicity may be derived from a calculation of the "hydrophobic moment", i.e., the measure of the amphiphilicity perpendicular to the axis of a periodic peptide structure; this approach is described in Eisenberg (*Ann. Rev. Biochem.* 53:595, 1984; hereby incorporated by reference).

It has been shown that it is the charged character (i.e., amphiphilic, hydrophilic, or hydrophobic) and/or secondary structure of a protein, and not its particular amino acid sequence, which facilitates the protein's interaction with other charged (or hydrophobic) surfaces (see, e.g., Kaiser and Kezdy, *Science* 223:249, 1984). Accordingly, it is possible to design any number of peptide analogues, having different amino acid sequences, provided that the local charge distribution (and overall net charge) and secondary structure, and hence the biological activity (in this case, the ability to target vascular lesions) is maintained. Such peptide analogues will generally differ from the native protein sequences by conservative amino acid substitutions (e.g., substitution of Leu for Val, or Arg for Lys, etc.) well known to those skilled in the art of biochemistry. Moreover, peptides may be designed which include a region(s) of amphiphilic, hydrophobic, hydrophilic and/or secondary structure embedded within a longer amino acid stretch. Generally, the charged character and secondary structure of such a region is unaffected by the surrounding amino acid residues. Again, only those peptides which are capable of targeting vascular lesions are considered to be useful in the invention.

Good candidates for peptides useful in the invention are peptides based on surface-exposed protein domains (i.e., regions of the protein which are present on the external surface of a protein molecule, preferably a vascular-associated protein molecule) because such regions are most likely to interact with the vascular wall or with a vascular-associated extracellular component. The identity of surface-exposed domains may be determined by tryptic digest analysis (see below) and/or by calculation of a region's degree of hydrophobicity/hydrophilicity (e.g., by the Chou-Fasman method, *Ann. Rev. Biochem.* 47:251, 1978); extracellular domains are generally hydrophilic or amphiphilic in character; such domains are frequently surrounded by hydrophobic stretches which correspond to transmembrane domains.

The peptides, once designed, can be synthesized by any of a number of established procedures, including, e.g., the expression of a recombinant DNA encoding that peptide in an appropriate host cell. Alternatively, these peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. The peptides so synthesized are then labelled with a reagent which enables the monitoring of the peptide after its administration to a patient.

Peptides may be tested for their ability to effectively target vascular lesions using an in vivo animal assay (e.g., that assay described herein). It is known that LDL accumulates both in the balloon de-endothelialized healing arterial wall of the rabbit and in human atheroma (Roberts et al., *J. Lipid Res.* 24:1160, 1983; Lees et al., *J. Nuclear Med.* 24:154, 1983). Accordingly, a rabbit whose abdominal aorta has been balloon de-endothelialized approximately four weeks prior may be used as a test model for human arterial disease. Other animals or experimental systems can be used as well, such as Watanabe Heritable Hyperlipemic rabbits which have inherited high blood cholesterol secondary to a deficiency in LDL receptors. This strain of rabbit develops spontaneous atherosclerosis at about 2 months of age, and they often die of heart attacks.

The rabbit model has been imaged both by onlay autoradiography with $^{125}$I-labelled LDL and by external imaging with $^{99m}$Tc-labelled LDL using a gamma scintillation camera. In each case, onlay autoradiography of the excised rabbit aorta has been reliably predictive of the in vivo results with extracorporeal imaging. In preparation for vascular administration, each labelled synthetic peptide may be injected in the free state or, alternatively, may be bound to the surface of a lipid emulsion such as a cholesterol ester phospholipid microemulsion. The emulsion is then injected intravenously into the rabbit. Approximately twenty-four hours later, the rabbit is subjected to extracorporeal monitoring appropriate for the specific label on the peptide. Alternatively, the rabbit is sacrificed, and its aorta removed and washed. The aorta is either cut into sequential portions which are then monitored in a liquid scintillation counter, or is dried, covered with a layer of polyester wrap, and placed on a sheet of x-ray film which is then developed to produce an onlay autoradiogram after suitable storage time in the dark.

Use

The peptides of the invention may be used to diagnose vascular injury or, alternatively, to inhibit binding of LDL to vascular walls. In either case, the peptide is first administered to a subject, e.g., a patient. Administration may be accomplished by arterial or venous injection. Alternatively a non-hydrolyzable derivative of the peptide (e.g., a keto methylene derivative) may be administered by mouth, or administration may be accomplished nasally.

In preparation for vascular administration, labelled synthetic peptide is suspended in a pharmaceutically-acceptable carrier (e.g., a physiological saline solution) or alternatively may be bound to the surface of a lipid emulsion such as a cholesterol ester phospholipid microemulsion (MV), and the emulsion is then injected intravenously.

For diagnostic use, the labelled peptide is administered in an amount sufficient for later detection (generally, 0.5–1 mg intravenously or 5–100 mg orally). In preferred embodiments of the invention, the peptide is labelled with, e.g., a radioisotope such as $^{123}$I, I or $^{99m}$Tc, and peptide accumulation at a site of injury imaged extracorporeally by radiation detection means such as a gamma scintillation camera; alternatively, the synthetic peptide is labelled with a non-radioactive, paramagnetic contrast agent capable of being detected in MRI systems. In such systems, a strong magnetic field is used to align the nuclear spin vectors of the atoms in a patient's body. The field is then disturbed and an image of the patient is read as the nuclei return to their equilibrium alignments. In the present invention, synthetic peptides can be linked to paramagnetic contrast agents such as gadolinium, cobalt, nickel, manganese or iron complexes, to form conjugate diagnostic reagents that are imaged extracorporeally with an MRI system.

For treatment of vascular disease (i.e., to inhibit LDL binding to vascular walls), the peptide is administered in a therapeutically-effective dose, generally 5–100 mg intravenously or intramuscularly. Treatment may be repeated, as necessary, to prevent or alleviate vascular damage.

DESCRIPTION OF THE PREFERRED EMBODIMENTS

There now follows a description of the design and synthesis of sample peptides useful in the invention. There also follows a description of an in vivo assay used to test the ability of such peptides to target vascular injury. These examples are provided to illustrate the invention and should not be construed as limiting.

Apolipoprotein Peptides

Apoliprotein B (apoB) is the protein moiety of low density lipoprotein. The primary structure of apo B-100 has become available by virtue of its cloning (see e.g., Knott et al., *Nature* 323:734–742, 1986; Yang et al., *Nature* 323:738, 1986; Carlsson et al., *Nucl. Acids Res.* 13:8813, 1985). Further, enzymatic treatment of apo B-100 with trypsin has enabled the identification of those surface regions which are apparently involved in the binding of LDL to various cells and tissues (Forgez et al., *Biochem. Biophys. Res. Comm.* 140:250, 1986; Knott et al., *Nature* 323:734, 1986). The surface-exposed regions are shown schematically in FIG. 1. The amino acid sequence analyses of representative tryptic peptides are shown in TABLE 1.

TABLE 1*

| HPLC Fraction No. (Tp) | Amino Acid Sequence | Corresponding to Apo B Amino Acid Residue Nos.[a] |
|---|---|---|
| 24 | (Lys)—Phe—Val—Thr—Gln—Ala—Glu—Gly—Ala—Lys SEQ ID NO: 18 | 1008–1016 |
| 123 | (Lys)—Leu—Pro—Gln—Gln—Ala Asn—Asp—Tyr—Leu—Asn—Ser—Phe—Asn—Asn—Glu—Arg SEQ ID NO: 19 | 2091–2106 |
| 70 | Leu—Pro—Gln—Gln—Ala—Asn—Asp—Tyr SEQ ID NO: 20 | 2091–2098 |
| 49 | (Lys)—Phe—Arg—Glu—Thr—Leu—Glu—Asp—Thr—Arg SEQ ID NO: 21 | 2485–2493 |

TABLE 1*-continued

| HPLC Fraction No. (Tp) | Amino Acid Sequence | Corresponding to Apo B Amino Acid Residue Nos.[a] |
|---|---|---|
| 99 | (Arg)—Ile—Ser—Leu—Pro—Asp— Phe—Arg SEQ ID NO: 22 | 2679–2685 |
| 161 | (Arg)—Thr—Phe—Gln—Ile—Pro Gly—Tyr—Thr—Val—Pro—Val—Val— Asn—Val—Glu—Val—Ser—Pro—Phe SEQ ID NO: 22 | 3218–3236 |
| 134 | Tyr—Thr—Val—Pro—Val—Val—Asn— Val—Glu—Val—Ser—Pro—Phe—Thr— Ile—Glu—Met—Ser—Ala—Phe—(Gly— Tyr—Val—Phe—Pro—Lys) SEQ ID NO: 23 | 3224–3232 |
| 184 | (Arg)—Val—Pro—Ser—Tyr—Thr— Leu—Ile—Leu—Pro—(Ser—Leu—Glu— Leu—Pro—Val—Leu—His—Val—Pro— Arg) SEQ ID NO: 24 | 3265–3275 |
| 59 | (Lys—Ile—Ala—Asp—Phe—Glu—Leu— Pro—Thr)—Ile—Ile—Val—Pro—Glu— Gln—Thr—Ile—Glu—Ile—Pro—Ser- 7-Ile SEQ ID NO: 25 | 3828–3841 |
| 106 | (Arg)—Asn—Leu—Gln—Asn—Asn— Ala—Glu—Trp—Val—Tyr—Gln—Gly— Ala—Ile—Arg SEQ ID NO: 26 | 4080–4094 |

[a] Residue numbers taken from the complete primary sequence of apolipoprotein B.
*from Forgez et al., ibid.

Based on the data of Forgez et al. (ibid) the published apo B sequence (described above), and information known to those skilled in the art of biochemistry and peptide design (e.g., that described above), synthetic peptides having an amino acid sequence analogous to the amino acid sequences of surface regions of the apo B moiety of LDL were designed. In some cases, the peptides were amidated at their carboxy terminus and/or acetylated at their amino terminus (i.e., the "A" or "a" peptides). Nine representative apo B peptides and their modified counterparts are shown below. The numbers above the amino acid residues refer to the primary sequence of apo B.

SP-4:

```
                           1008
NH2-Tyr-Arg-Ala-Leu-Val-Asp-Thr-Leu-Lys-Phe-Val-Thr-

1016
  Gln-Ala-Glu-Gly-Ala-Lys-CONH2;
```

SP-4A:

```
                                     1008
CH3CONH-Tyr-Arg-Ala-Leu-Val-Asp-Thr-Leu-Lys-Phe-Val-      SEQ ID NO:1;

1016
  Thr-Gln-Ala-Glu-Gly-Ala-Lys-CONH2
```

SP-6:

```
     1000
HN2-Tyr-Lys-Leu-Ala-Leu-Glu-Ala-Ala-Arg-Leu-Leu           SEQ ID NO:2

1010
  Ala-Asp-Ala-Glu-Gly-Ala-Lys-CONH2;
```

SP-6A:

```
        1000
CH3CONH-Tyr-Lys-Leu-Ala-Leu-Ala-Leu-Glu-Ala-Ala-Arg-Leu-  SEQ ID NO:2

1010
Leu-Ala-Asp-Ala-Glu-Gly-Ala-Lys-CONH2;
```

SP-8:

```
           1000
H₂N-Tyr-Lys-Leu-Ala-Leu-Glu-Ala-Ala-Arg-Leu-Leu-          SEQ ID NO:3

1010
    Ala-Asn-Ala-Glu-Gly-Ala-Lys-CONH₂;
```

SP-8A:

```
               1000
CH₃CONH-Tyr-Lys-Leu-Ala-Leu-Glu-Ala-Ala-Arg-Leu-Leu        SEQ ID NO:3

1010
    Ala-Asn-Ala-Glu-Gly-Ala-Lys-CONH₂;
```

SP-12A:

```
                                   1008
CH₃CONH-Tyr-Arg-Ala-Leu-Val-Asp-Tyr-Leu-Lys-Phe-Val         SEQ ID NO:4

Thr-Gln-Leu-CONH₂;
```

SP-14A:
```
CH₃CONH-Tyr-Arg-Ala-Leu-Val-Asp-Thr-Leu-Lys-CONH₂           SEQ ID NO:5;
```

SP-15a:

```
              2485
CH₃CONH-Tyr-Ala-Lys-Phe-Arg-Glu-Thr-Leu-Glu-Asp-Thr-Arg-    SEQ ID NO:6

2495
Asp-Arg-Met-Tyr-CONH₂;
```

SP-17:

```
            3810
H₂N-Tyr-Ala-Ala-Leu-Asp-Leu-Asp-Leu-Asn-Ala-Val-Ala-Asn-   SEQ ID NO:7
Lys-Ile-

3822
Ala-Asp-Phe-Glu-Leu-CONH₂;
```

SP-19a:

```
                                   1008
CH₃CONH-Tyr-Arg-Ala-Leu-Val-Asp-Thr-Leu-Lys-Phe-Val-Thr-   SEQ ID NO:8

Glu-Gln-Ala-Lys-Gly-Ala-CONH₂;
``` and

SP-21a:

```
              1002
CH₃CONH-Tyr-Arg-Ala-Leu-Val-Asp-Thr-Glu-Phe-Lys-Val-Lys-   SEQ ID NO:9

Gln-Glu-Ala-Gly-Ala-Lys-CONH₂.
```

Amino acids 2–13 of the apo B peptide, SP-4, were conservatively substituted, hydrophobic residue for hydrophobic residue, and charged residue for residues having the same charge to produce SP-6 and SP-8. SP-12 is a truncated form of SP-4 in which the last five amino acid residues were replaced with a single leucine (Leu) residue. SP-14 is a truncated form of SP-12 in which the last five amino acid residues have been deleted and the tyrosine (Tyr) residue at position 7 replaced with a threonine (Thr) residue. SP-15a and SP-17 include amino acids 2483–2497 (i.e., including Tp 49) and amino acids 3809–3825, (i.e., including part of Tp 59), respectively. The sequences of SP-19a and SP-21a are variations on the sequence of SP-4. Physical data obtained for peptides SP15a, SP17, SP19a, and SP21a are summarized in Table 2. Helical wheel diagrams demonstrating the amphiphilic and α-helical nature of these peptides are shown in FIG. 2; hydrophobic residues are encircled and charged residues are indicated. Abbreviations are : A, alanine; D, aspartate; E, glutamate; F, phenylalanine; G, glycine; K, lysine; L, leucine; N, asparagine; Q, glutamine; R, arginine; T, threonine; V, valine; Y, tyrosine; Ac, acetyl.

Another amphiphilic peptide (i.e., SP34a) was synthesized based on an apo A-I consensus peptide (termed APOA-I CONSENSUS), i.e., an idealized α-helix derived from a number of regions of apolipoprotein A-I; the sequence of this consensus peptide is published in Anantharamaiah (Meth. Enzymol. 128:630, 1986). Unlike apolipoprotein A-I, the synthetic peptide is only weakly charged, and the sequence is preceded by an amino-terminal tyrosine residue. This peptide was amidated at its carboxy terminus and acetylated at its amino terminus. This peptide has a weak net negative charge (i.e., –2; see Table 2).

SP-34a:

CH₃CONH-Tyr-Val-Leu-Asp-Glu-Phe-Arg-Glu-Lys-Leu-Asn-Glu-Glu-Leu-Glu-Ala-Leu-Lys-Gln-Lys-CONH 2 SEQ ID NO:10.

Physical data obtained for SP-34a are summarized in Table 2. A helical wheel diagram of SP-34a is shown in FIG. 2 (described above).

TABLE 2

| Peptide | Protein | MW[a] | Parent Protein <H>[b] | Charge[c] |
|---|---|---|---|---|
| SP-15a | apo B | 2135.0/2135.5 | −0.53 | 0 |
| SP-17 | apo B | 1950.0/1950.1 | 0.26 | −1 |
| SP-19a | apoB | 2051.1/2051.0 | 0.00 | +1 |
| SP-21a | apoB | 2094.1/2094.4 | −0.18 | +1 |
| SP-34a | apo A-I | 2535.3/2535.4 | −0.29 | −2 |
| SP-28 | elastin | 1622.9/1622.9 | 0.62 | −1 |
| SP-30 | elastin | 1818.0/1818.1 | 0.63 | +1 |
| SP-29 | elastin | 1408.8/1408.8 | 0.62 | +1 |

[a]Molecular weight (calculated/observed); expressed as the parent ion (M + H)$^+$, as determined by Fast Atom Bombardment Mass Spectrometry.
[b]Mean Hydrophobicity; calculated using the method and scale of Eisenberg (J. Mol. Biol. 279:125, 1984).
[c]Charge is expressed as the difference between positively and negatively charged groups on the peptide at neutral pH.

Elastin Peptides

Elastin is a major component of skin, arteries, lung, and other tissues (Rosenbloom; Robert and Robert, Frontiers of Matrix Biology, Vol. 8: *Biology and Pathology of Elastic Tissues*, 1980; Reddi, Extracellular Matrix: Structure and Function, 1985). Analysis of various elastin sequences (see Rosenbloom, *Meth. Enzymol.* 144:172, 1987) indicates that elastin proteins are generally composed of a number of repeated units. Two such repeated units are the pentapeptide, Val-Pro-Gly-Val-Gly (VPGVG) SEQ ID NO: 15, and the hexapeptide, Val-Gly-Val-Ala-Pro-Gly (VGVAPG) SEQ ID NO: 16. Structurally, elastin repeats have been shown, by circular dichroism (Rahman et al., *Coll. Czech. Chem. Comm.* 52:1356, 1987) and by extensive nuclear magnetic resonance studies (Urry et al., *Biopolymers* 25:1939, 1986), to contain repeating β-turn structures (*Biochem. Biophys. Res. Comm.* 153:832, 1988). The hexapeptide has chemotactic properties (Senior et al., *J. Cell. Biol.* 99:870, 1984).

Elastin-derived peptides useful for targeting arterial lesions include a hydrophobic binding site; this binding site facilitates interaction with a hydrophobic extracellular vascular wall component (e.g., elastin) and/or allows interaction of the peptide with the negatively-charged vascular wall. To facilitate solubility in physiological fluids, the peptides preferably include a hydrophilic domain or a net positive or weak negative charge.

Three representative elastin peptides are shown below. SP-28 includes three repeats of the elastin hexapeptide VGVAPG. SP-30 and SP-29 include four and three repeats, respectively, of the elastin pentapeptide VPGVG. The SP-30 and SP-29 peptides were amidated at their carboxy terminus.

SP-28:

H$_2$N-Tyr-Val-Gly-Val-Ala-Pro-Gly-val-Gly-Val-Ala-Pro-Gly-Val-Gly-Val-Ala-Pro-Gly-OH SEQ ID NO: 14;

SP-30:

H$_2$N-Tyr-Val-Pro-Gly-Val-Gly-Val-Pro-Gly-Val-Gly-Val-Pro-Gly-Val-Gly-Val-Pro-Gly-Val-Gly-CONH$_2$ SEQ ID NO; 13; and

SP-29

H$_2$N-Tyr-Val-Pro-Gly-Val-Gly-Val-Pro-Gly-Val-Gly-Val-Pro-Gly-Val-Gly-CONH$_2$ SEQ ID NO: 17.

Physical data obtained for elastin peptides is summarized in Table 2.

Peptide Synthesis and Labelling

Peptides SP-4, SP-4A, SP-6, SP-6A, SP-8, SP-8A, SP-12A, and SP-14A were synthesized by solid phase peptide synthesis according to the established method of Stewart and Young (*Solid Phase Peptide Synthesis*, 2nd ed., pp. 53–123, 1984 The Pierce Chemical Co., Rockford, Ill., hereby incorporated by reference). These peptides were synthesized using the schedule listed in TABLE 2, but any one of the other schedules listed in this reference may alternatively be used to generate any desired peptides (e.g., any peptide described herein).

TABLE 2

SCHEDULE FOR SOLID PHASE PEPTIDE SYNTHESIS
(Dioxane-HCl Deprotection: DCC Coupling)

| Step | Reagent | No. Repeats | Vol (ml) | Time(min.) |
|---|---|---|---|---|
| 1 | dry CH$_2$Cl$_2$ | 4 | 25 | 1 |
| 2a | 50% TFA** | 1 | 25 | 1 |
| 2b | 50% TFA | 1 | 25 | 20 |
| 3 | dry CH$_2$Cl$_2$ | 2 | 25 | 1 |
| 4 | dry 2-propanol | 2 | 25 | 1 |
| 5 | CH$_2$Cl$_2$ | 3 | 25 | 1 |
| 6 | 5% DIEA* | 1 | 25 | 2 |
| 7 | CH$_2$Cl$_2$ | 2 | 25 | 1 |
| 8 | 5% DIEA | 1 | 25 | 2 |
| 9 | CH$_2$Cl$_2$ | 5 | 25 | 1 |
| 10 | Introduce symmetric anhydride of Boc AA** | 1 | 20 | 20 |
| 11 | TFE#/DIEA/ CH$_2$Cl$_2$(add) | 1 | 5 | 10 |
| 12 | CH$_2$Cl$_2$ | 3 | 25 | 1 |
| 13 | 100% EtOH | 3 | 25 | 1 |

*dicyclohexylcarbodiimide
**trifluoroacetic acid
*diisopropylethylamine
**tert-butytoxycarbonyl amino acid
2,2,2-trifluoroethanol Peptides SP-15a, SP-17, SP-19a, SP-21a, SP-34a, SP28, SP-30 and SP-29 were synthesized by manual solid-phase methods using tert-butoxycarbonyl (t-Boc)-based chemistry. (Barany and Merrifield, *The Peptides: Analysis, Synthesis, Biology*, Academic Press, New York, 1980; Stewart and Young, *Solid-Phase Peptide Synthesis*, 2nd ed., Pierce Chemical Co., Rockford, Ill., 1984). Sidechain protecting groups for amino acid derivatives included: benzyl esters for Asp and Glu, benzyl ethers for Ser and Thr, chlorobenzyloxycarbonyl for Lys, bromobenzyloxy for Tyr, and mesitylenesulfonyl for Arg. The carboxyl terminal amino acid residue was attached to methylbenzhydrylamine resin with diisopropylcarbodiimide (DIC) by the method of Stewart and Young (supra). The peptide resin was washed twice with CH$_2$Cl$_2$ and once with 50% TFA in CH$_2$Cl$_2$/1% dimethylsulfide, and the t-Boc group was removed by treatment for 20 minutes with 50% TFA in CH$_2$Cl$_2$/1% dimethylsulfide, or by treatment with 25% TFA in CH$_2$Cl$_2$/1% dimethylsulfide for 30 minutes. The peptide resin was next washed five times with 5× CH$_2$Cl$_2$; neutralized with two washes of 10% diisopropylethylamine (DIEA) in CH$_2$Cl$_2$; and washed five times with CH$_2$Cl$_2$. The next amino acid was coupled by treatment with either three equivalents of symmetrical anhydride (see below) for 45 minutes or four equivalents of active ester (see below) for 2 hours, in the presence of 1.5 equivalents of DIEA. The peptide resin was then washed four times with CH$_2$Cl$_2$; twice with 33% ethanol in CH$_2$Cl$_2$; and twice with CH$_2$Cl$_2$.

Symmetrical anhydride-activated amino acids were prepared by treating 6.1 equivalents of amino acid with three equivalents of DIC in CH$_2$Cl$_2$ for 20 minutes, on ice. Active esters of hydroxybenzotriazole (HOBt) were prepared from four equivalents each of amino acid, HOBt, and DIC in dimethyl formamide (DMF) for 30 minutes on ice. Active esters of ethylhydroxyiminocyanoacetate (EACNOx) were prepared from four equivalents each of amino acid, EACNOx, and DIC in $CH_2Cl_2$ for 30 minutes, on ice. Completion of coupling at each step was verified by the Kaiser ninhydrin test (Kaiser et al., *Anal. Biochem.* 34:595, 1970). Incomplete couplings were repeated once or twice and, if still incomplete, the peptide resin was acetylated with acetic anhydride prior to continuation of synthesis. Peptides were deprotected and cleaved from the resin either by HF-treatment (performed as directed by Immunodynamics, San Diego, Calif.) or by treatment with 1:10:1:0.5 trifluoromethanesulfonic acid:TFA:thioanisole:ethanedithiol by the method of Yajima et al. (*J. Chem. Soc., Chem. Comm.* p.107–108, 1974). Crude deprotected peptides were either desalted on a column of Sephadex G-25 eluted with 5% acetic acid or were precipitated twice from the TFA solution with 10 to 100 volumes of ethyl ether. Peptides were then purified by reverse-phase HPLC using a Vydac $C_{18}$ column and a gradient of 0%–90% $CH_3CN/H_2O$ containing 0.1% TFA. Solutions of purified peptides were evaporated, redissolved in water, and lyophilized to dryness. Identity of peptides was confirmed by Fast Atom Bombardment Mass Spectrometric (FAB-MS) analysis.

The synthetic peptides SP-4, SP-4A, SP-6, SP-6A, SP-8, SP-8A, SP-12A, and SP-14A were radiolabelled by the chloramine T method as described in Shih et al. (*Proc. Natl. Acad. Sci. USA* 87:1436, 1990, herein incorporated by reference). Certain experiments required radiolabelled LDL. In these cases LDL was labelled with $^{125}$-iodine by a previously described modification of the McFarlane iodine monochloride technique described in Lees et al. (*Proc. Natl. Acad. Sci. USA* 80:5098, 1983, hereby incorporated by reference). The radiolabelled lipoprotein or synthetic peptide was separated from unbound radioisotope by passage through a gel filtration "desalting" column of Sephadex G-25 or the equivalent.

The synthetic peptides SP-15a, SP-17, SP-19a, SP-21a, SP-34a, SP-28, SP29, and SP30 were radiolabelled with $^{125}I$ using chloramine-T as follows.

The peptide (400 µg) was dissolved in 200 µl of 2.5 mM sodium phosphate/37.5 mM NaCl buffer, pH 7.4 and mixed with 1 mCi (3 µl) $^{125}I$. Chloramine-T (30 µl, 8 mg/ml in $H_2O$) was added to the mixture and, after 35 seconds, the reaction was quenched by the addition of sodium bisulfite (60 µl, 8 mg/ml). Radiolabeled peptides were gel-filtered on a Bio-Gel P-2 (Bio-Rad, Hercules, Calif.) column (1 cm×30 cm) and eluted with 0.1% BSA in 0.1M acetic acid. A lead fraction of 5 ml was collected, followed by 0.45 ml fractions. Iodinated peptide, which eluted at approximately fractions 9–12, was pooled and the pH adjusted to 5 with 1N NaOH and then to 7.5 with 1M $NaHCO_3$.

Iodination of SP17 was performed essentially as described above except that the reaction mixture was adjusted to a final concentration of 50% ethanol. Following iodination, the radiolabeled peptide was precipitated by addition of bovine serum albumin to a final concentration of 10%, and the precipitate was collected by centrifugation at 2000 rpm for 15 minutes. The pellet was then washed four times with 1 ml. (each) of water and, after the final wash, the precipitate was dissolved in 5 ml. of 10% BSA. Alternatively, 20% BSA was added to the iodinated peptide (in 50% ethanol) to a final concentration of 10% and a volume not exceeding 5 ml. The solution was then passed through a BioGel P-2 (10 cm×1.5 cm) column and eluted with 0.1% BSA in 0.1M acetic acid as described above. Excess buffer was removed using nitrogen pressure, the column was washed with 5 ml of 0.1% BSA/ 0.1M acetic acid, and the most highly radioactive fractions pooled for injection.

In an alternative method, the synthetic peptides are labelled either directly with technetium (Tc), or indirectly through covalent attachment of a chelating group such as diethylenetriamine pentaacetic acid (DTPA), which is known to chelate a variety of metals including radioisotopes such as $^{111}$-indium.

Direct coupling to $^{99m}Tc$ is carried out as follows. 50 mCi $^{99m}Tc$ (in the form of $^{99m}\text{-}TcO_4^-$), in a 0.5 ml aqueous solution, is added to 1–6 mg, but preferably to 2 mg, synthetic peptide in 0.5 ml of a 0.2 M sodium bicarbonate solution, pH 8.0, and mixed thoroughly for 10 minutes at room temperature. The pH is raised to 8.0–9.0 if necessary with 0.25 M sodium hydroxide. To the mixture is then added 10 mg of reduced sodium dithionite (57.5 mmoles) freshly dissolved in 0.5 ml distilled water. The mixture is gently stirred for 30 minutes at room temperature.

The radiolabelled synthetic peptide fraction is separated from uncoupled technetium and sodium dithionite by molecular sieve chromatography. A 1×50 cm column of Sephadex G-25, equilibrated with a EDTA-bicarbonate buffer (0.2 M sodium bicarbonate, pH 8.0, 0.001 M EDTA), is suitable for separation. The column is standardized with blue dextran and potassium iodide to determine the void volume and the column volume, respectively. The reaction mixture is applied to the column, and bicarbonate-EDTA buffer is used to elute column fractions. The macromolecular radioactive peak that elutes at a position characteristic for the synthetic peptide is isolated and ready for use.

Indirect coupling to $^{99m}Tc$ is carried out as follows. A chelating ligand, e.g., DTPA (as per Hnatowich et al., *Science* 220:613, 1983) or bromoacetylparaaminobenzyl EDTA (BABE; as per Meares et al., *Analyt. Biochem.* 142:142, 1984) is covalently bound to the N- or C-terminus of the peptide. These references are hereby incorporated by reference. Technetium is then chelated to the DTPA- or BABE-synthetic peptide by the procedure described above for direct labelling of synthetic peptide. Technetium, in the form of $^{99m}TcO_4^-$ is added to the DTPA-synthetic peptide, and to the mixture is added a solution of reduced sodium dithionite, pH 8.0–9.0. $^{99m}Tc$-labelled synthetic-DTPA peptide is separated from uncomplexed $^{99m}Tc$ and sodium dithionite by column chromatography (as described above). The preparations are then characterized by silica gel chromatography essentially as described by Meares et al. (ibid.) and by HPLC. The $^{99m}Tc$-labelled peptide is administered either in a pharmaceutically-acceptable carrier solution or bound to a lipid emulsion.

Structure

To determine whether the molecular conformation or structure of the synthetic apoB peptides was analogous to the conformation of the apoB moiety of LDL, a polyclonal antiserum was raised to each peptide and its ability to bind LDL tested. Antiserum raised to human LDL was used as the control.

Specific anti-LDL antisera may be purchased from a number of sources (e.g., Hoechst Pharmaceutical, Inc., Cincinnati, Ohio and Marburg-Lahn, West Germany; and Hyland Laboratories, Inc., 4501 Colorado Boulevard, Los Angeles, Calif.). Alternatively, antisera may be prepared by any number of protocols known to those skilled in the art. For assays described herein, anti-LDL antiserum was produced as follows. 5–20 mg of LDL, prepared according to the method of Fischman et al. (*Arteriosclerosis* 7:361, 1987) in about 1 ml of saline or barbital buffer, was emulsified with an equal volume of Freund's complete adjuvant (Difco Laboratories, Detroit, Mich.). This was most easily done by placing the lipoprotein and the adjuvant in separate 5 ml Luer-Lock syringes with 20-gauge needles and connecting the two needles via a 1-inch piece of 0.030 inch inner diameter polyethylene tubing. The contents of the syringes are then forcefully expelled from one syringe into the other several dozen times through the two needles and the connecting tubing. A stable creamy emulsion was produced which was finally passed entirely into one of the syringes, and the connecting tubing is removed. The emulsified antigen was injected subcutaneously into the back of a laboratory rabbit. If several rabbits were to be injected with the same antigen, larger syringes and larger quantities of materials were used and each rabbit injected with 2 ml of the emulsion representing 1 ml of the original antigen solution. An alternative method for preparing emulsion in quantity is to place equal volumes of antigen solution and adjuvant into one tube of a Mickle disintegrator (Mickle Company, Hampton, Middlesex, England; Brinkmann Instruments, Inc., Westbury, N.Y.) which is stoppered and placed on one of the steel reeds of this magnetic vibrator. A second sample or a water balance is placed on the other reed, the machine turned on, and the reeds tuned to maximal excursion for about ten minutes. The resulting emulsion is drawn into syringes through a blunt 18-gauge needle and injected subcutaneously through 20-gauge needles.

For the preparation of antisera of high antibody titer the animal may be "boosted" every 3–5 weeks exactly as for the first injection. Good antiserum is usually obtained after two injections. Animals treated in this way may be maintained for long periods in the immune state and will yield very large amounts of antiserum. If quantities of antiserum in the range of 1 liter or more are needed, sheep may be used in the same manner, except that two to three times the amount of immunizing antigen is required. The animals are bled 6–10 days after each booster injection. A small test bleeding may be made to check the antibody level and purity if desired.

The blood is allowed to clot at room temperature for several hours and is then placed overnight in the refrigerator. The samples are centrifuged in the cold, the clots removed with an applicator stick, recentrifuged to sediment the remaining blood cells, and the serum is decanted. One milligram per milliliter of sodium azide is added as a preservative. Antisera in constant use may be kept in the refrigerator, or stored at −15° to −20° C.

To produce anti-synthetic peptide antisera, purified synthetic peptide was dissolved in PBS, pH 7.4 at a concentration of 1 mg/ml. The peptide solution was mixed with an equal volume of complete Freund's adjuvant and vortexed thoroughly until a thick emulsion was produced. New Zealand White rabbits (Millbrook Farms, Amherst, Mass.) were injected with a total of 0.5 mg synthetic peptide administered subcutaneously in the four dorsal quadrants. The rabbits were given a boost (injected at the same sites) with 0.5 mg peptide emulsified in incomplete Freund's adjuvant 2–3 weeks later. Eight to ten days after the first boost, the animals were given a second, identical boost and were bled of 30 ml 8 to 10 days later.

Figure 4:
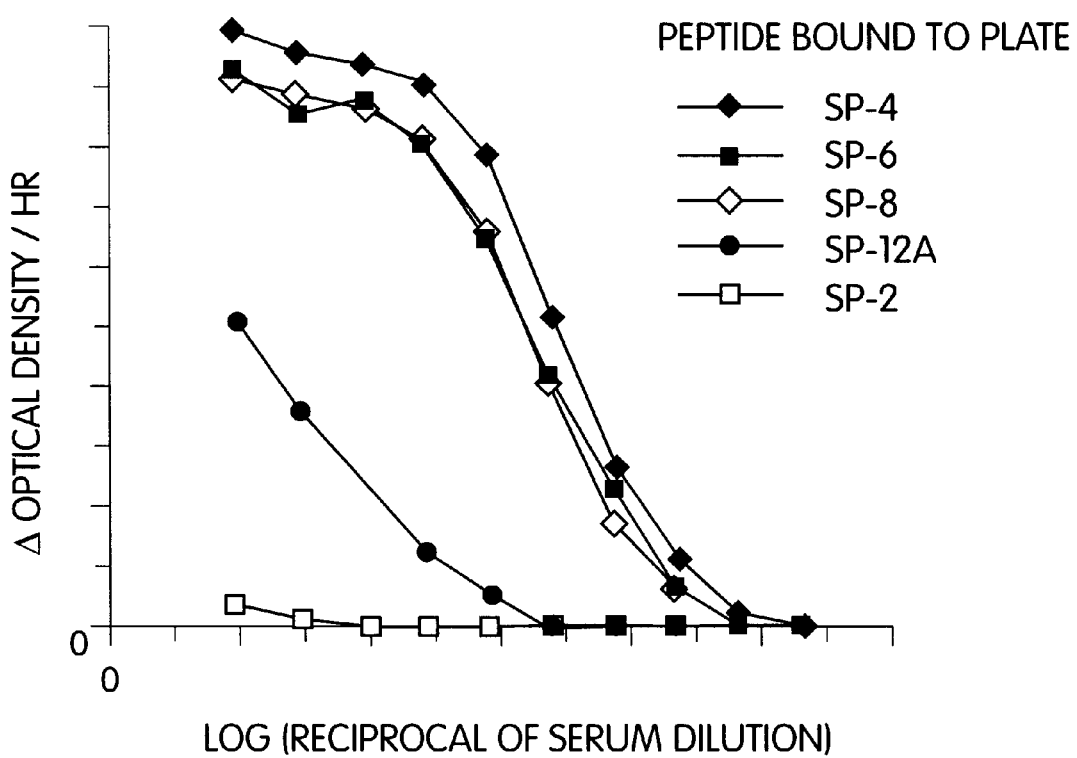
FIG. 4 is a graphic representation demonstrating the ability of anti-SP-4 antibody to bind to SP-4, SP-6, SP-8, and SP-12A.

To test for immunological cross-reactivity microtiter plates (Immulon II Dynatech Labs, Chantilly, Va.) were coated with the purified synthetic peptide or LDL by an overnight incubation at 4° C. with 100 ng peptide per well in 50 mM carbonate, pH 9.6, and blocked for nonspecific binding with an additional overnight incubation with phosphate-buffered saline, pH 7.4 (PBS), 1% bovine serum albumin (BSA). Control wells were coated with BSA alone. After washing twice with PBS, the wells were filled with serial dilutions (1:10 to 1:100,000 made in PBS, 3% BSA) of a rabbit polyclonal antibody generated against the synthetic peptide(s) and incubated for 45 minutes at room temperature. Following thorough washing (3× with PBS, 0.1% BSA), the wells were filled with a 1:2000 dilution of goat anti-rabbit IgG-horseradish peroxidase conjugate (Atlantic Antibodies, Scarborough, Me.). After a final wash, the wells were filled with 3,3'-5,5'-tetramethybenzidine (TMB) microwell peroxidase substrate (Kirkegaard and Perry Labs, Gaithersburg, Md.) and read at 650 nm every two minutes on an ELISA-5 automated plate reader (Physica, New York, N.Y.). Results (see, e.g., FIGS. 4 and 5) are expressed as the initial velocity of substrate conversion (change in $OD_{650}$/hr), which is determined by a linear regression of 15 data points per well. Each data point represents the average of three measured data points from the same plate, run at the same time.

Figure 3:
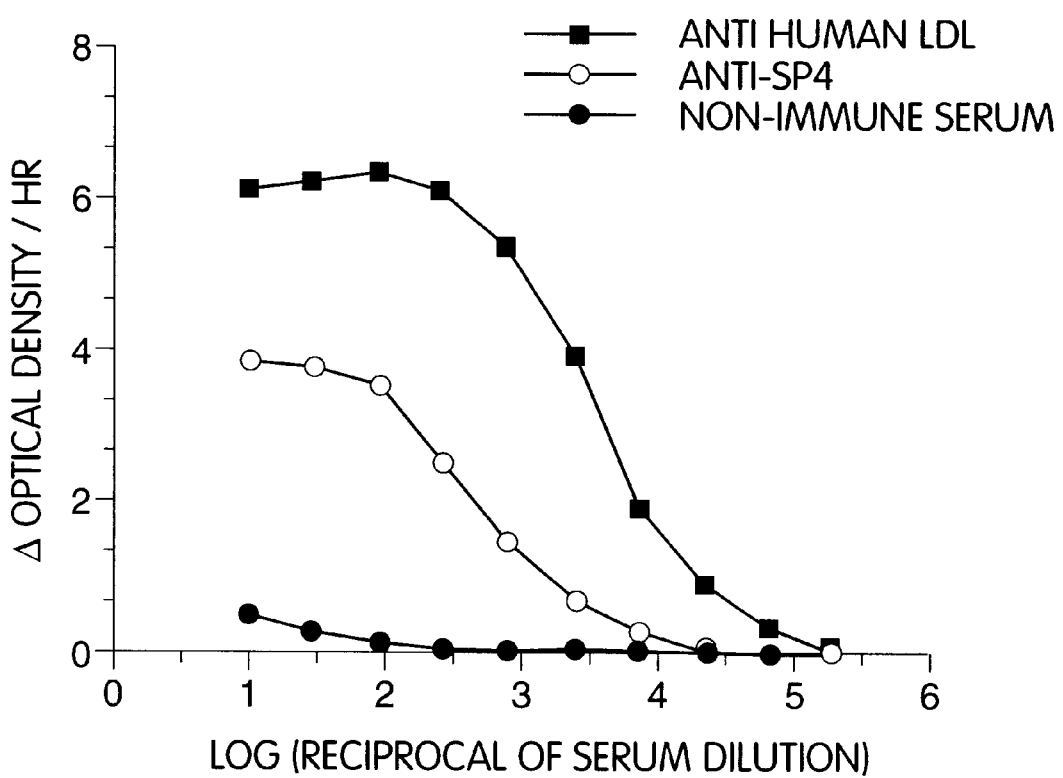
FIG. 3 is a graphic representation of the binding of anti-SP-4 antibody to LDL.

FIG. 3 shows ELISA plates coated with LDL and treated with SP-4 antiserum. Anti-SP-4 antiserum was able to bind LDL on the plates, providing immunological confirmation that SP-4 and LDL have structural similarities. In analogous experiments, shown in FIG. 4, anti-SP-4 antiserum was shown to bind SP-4 and SP-4A as well as the conservatively substituted peptides, SP-6, SP-6A, SP-8, SP-8A, SP-12A, and SP-14A, demonstrating that these peptides have structural similarities to SP-4.

Animal Model:

The peptides described herein were assayed for their ability to target sites of vascular injury as follows. Male New Zealand white rabbits (2 to 3 kg each) were obtained from ARI Breeding Labs, West Bridgewater, Mass. To induce vascular injury, their abdominal aortas were denuded of endothelium by a modification of the Baumgartner technique (Fischman et al., *Arteriosclerosis* 7:361, 1987). Briefly, after each animal was anesthetized with ketamine and ether or, alternatively, with xylazine (20 mg/ml) and Ketalar (50 mg/ml), the left femoral artery was isolated; a 4F Fogarty embolectomy catheter (Model 12-040-4F, Edwards Laboratories Incorporated, Santa Anna, Calif.) was introduced through an arterotomy in the femoral artery and was advanced under fluoroscopic visualization to the level of the diaphragm. The catheter was inflated to a pressure of about 3 psi above the balloon inflation pressure with radiographic contrast medium (Conray, Mallinkrodt, St. Louis, Mo.). Three passes were made through the abdominal aorta with the inflated catheter to remove the aortic endothelium before removal of the catheter, ligation of the femoral artery, and closure of the wound. The animals were allowed to heal for a period of 4 to 5 weeks before injection of the labelled synthetic peptides.

Watanabe Heritable Hyperlipemic (WHHL) rabbits were also used as animal models. They were obtained from the WHHL Rabbit Program of the National Heart Lung and Blood Institute (Bethesda, Md.) at about 3 months of age and weighing about 1.5 kg. The animals were raised until they were 3–4 kg in weight. At this weight, they exhibited marked aortic atherosclerosis.

Figure 5:
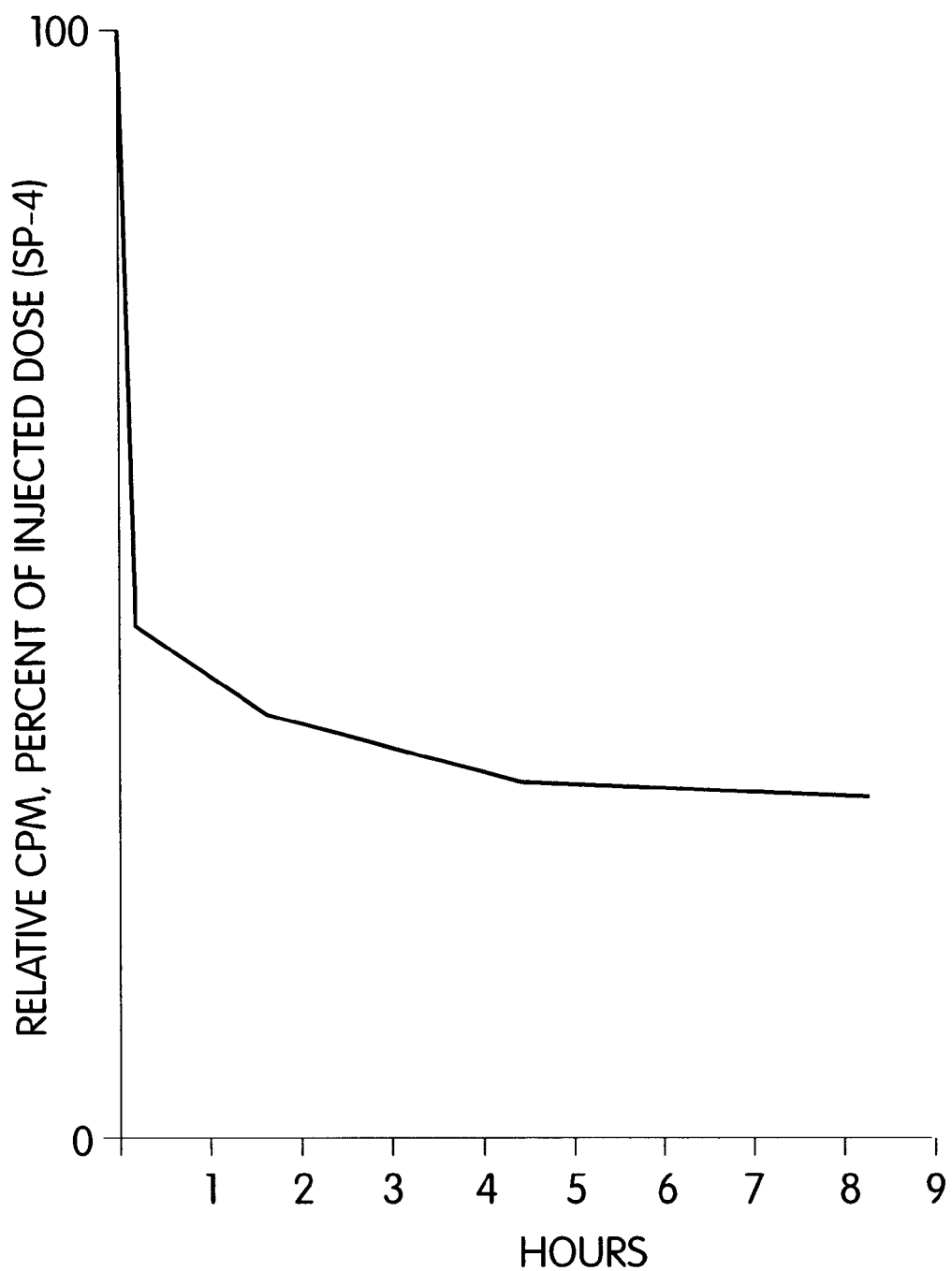
FIG. 5 shows a representative plasma decay curve for $^{125}$I-labelled synthetic peptide.

Each labelled synthetic peptide preparation (containing, for example, 150 to 400 or more $\mu$Ci of $^{125}$I-labelled peptide) in column elution buffer was injected into the marginal ear vein of the ballooned and healing New Zealand white rabbits or WHHL rabbits. Serial blood samples were obtained from the opposite ear during the ensuing 0–24 hours and were analyzed for radioactivity. The labelled peptide concentrations in the blood samples that were withdrawn over the first 10 minutes after injection were extrapolated to zero time to determine the time zero radioactivity in the calculation of average plasma radioactivity. FIG. 5 shows a plasma decay curve for the representative $^{125}$I- labelled synthetic peptide SP4. Peptides SP15a, SP17, SP19a, SP21a, SP28, SP34a, and SP30 were cleared rapidly from the plasma with half-lives of about one minute or less; after one hour, the plasma levels were less than 10% of the injected dose and fell by an additional 1% over the next three hours. Peptides SP15a, SP17, SP21a, SP28, SP34a, and SP30 leveled off to a plasma level of 3–6%; peptide SP19a cleared more quickly and leveled off to a concentration of 0.3% (at four hours).

One to twenty-four hours after injection of the labelled synthetic peptide preparations, each animal was injected intravenously with 4 ml of a 0.5% solution of Evans blue dye (Allied Chemical Company, National Aniline Division, New York, N.Y.) which stains areas of de-endothelialized aorta blue. After 30 minutes, the animal was sacrificed by a lethal injection of pentobarbital. After sacrifice, the aorta was removed completely, washed in saline, and fixed in 10% trichloroacetic acid.

The washed and fixed aortas from the animals that had been injected with radiolabelled synthetic peptide were opened along the ventral surface. These segments were then pinned out, fixed for 2 hours in 10% trichloroacetic acid, and photographed. The fixed, opened vessels were then covered with a single layer of plastic (Saran) wrap, placed on high speed x-ray film (Kodak Orthofilm OH-1), and stored for 3 days to 4 weeks in a Kodak "X-Omatic cassette" (24×30 cm) at −70° C. before development in a 90 second X-OMAT.

Figure 6:
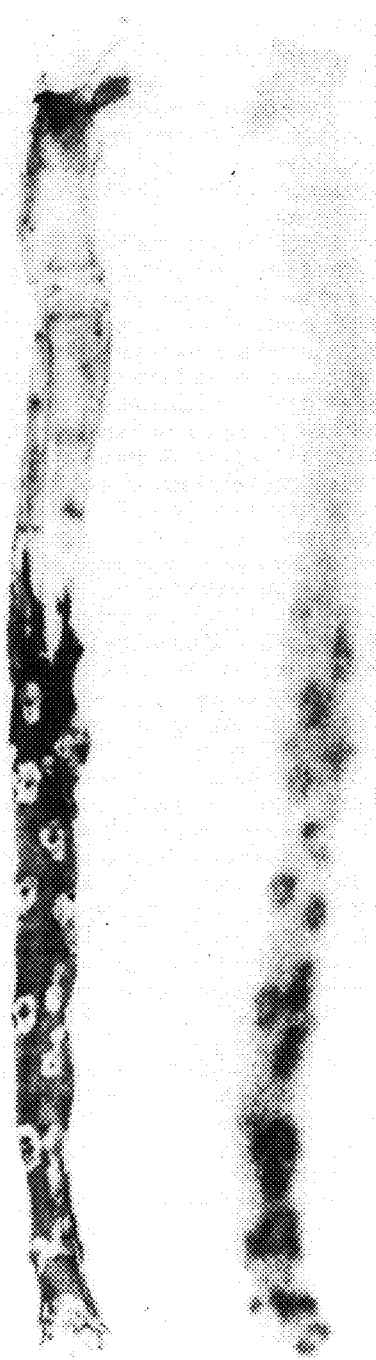
FIG. 6 is an onlay autoradiograph of the abdominal aorta of a rabbit which has been injected in vivo with 125I-labelled synthetic peptide SP-4, showing labelled healing lesions in the balloon de-endothelialized section of the aorta (B) as compared with the unlabelled control portion (A).
Figure 7:
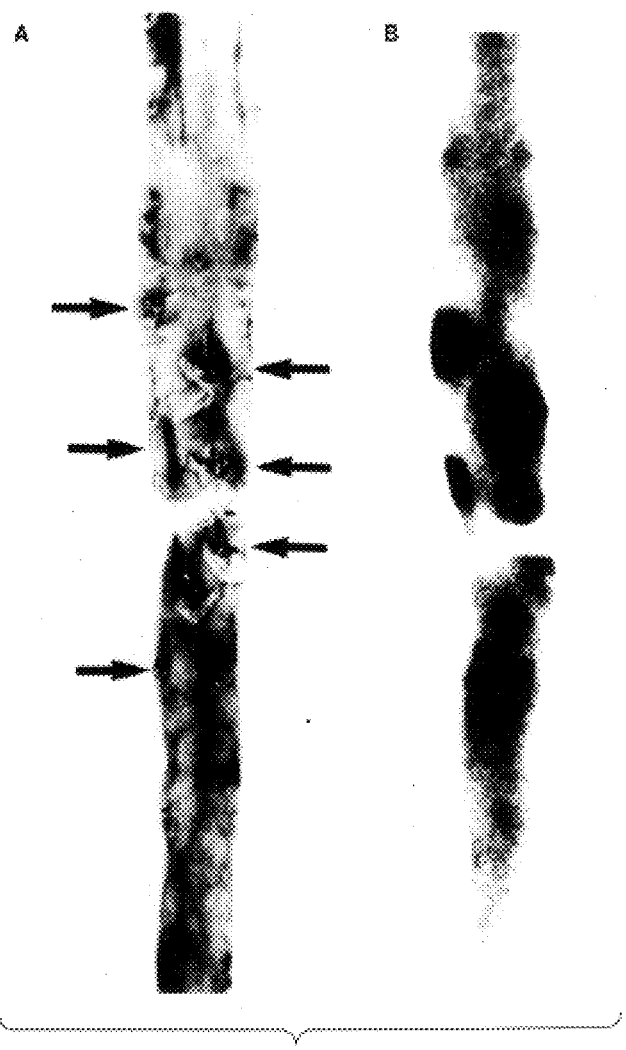
FIG. 7 shows a photograph (A) and an onlay autoradiograph (B) of the abdominal aorta of a rabbit treated with $^{125}$I-labelled synthetic peptide SP-4, demonstrating that the peptide localizes at atherosclerotic lesions.
Figure 8A:
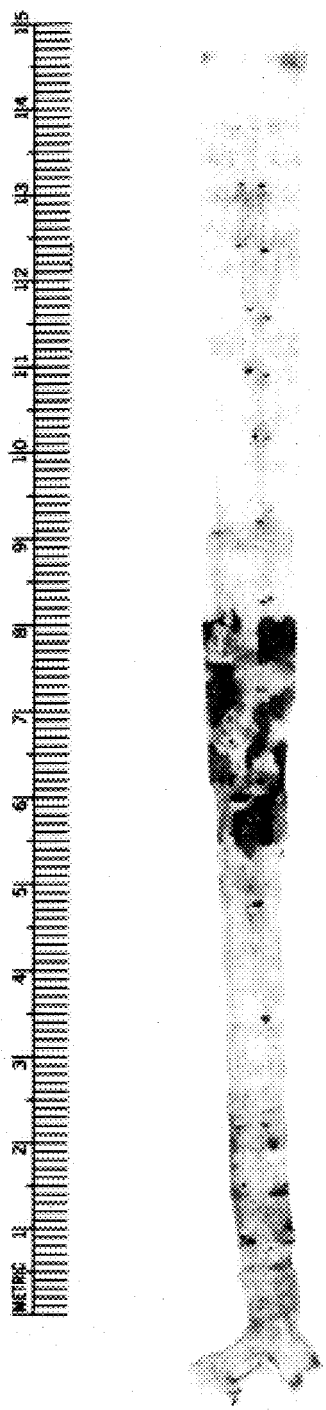
FIG. 8 shows a photograph (A) and an onlay autoradiograph (B) of the abdominal aorta of a rabbit treated with $^{125}$I-labelled synthetic peptide, SP-17.
Figure 8B:
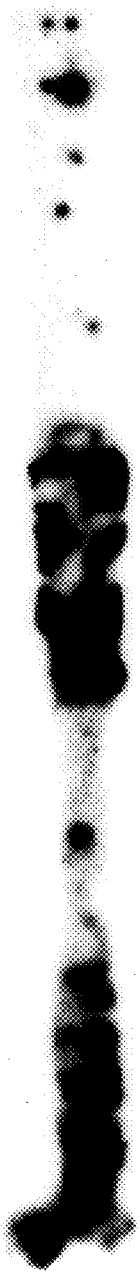
Figure 10A:
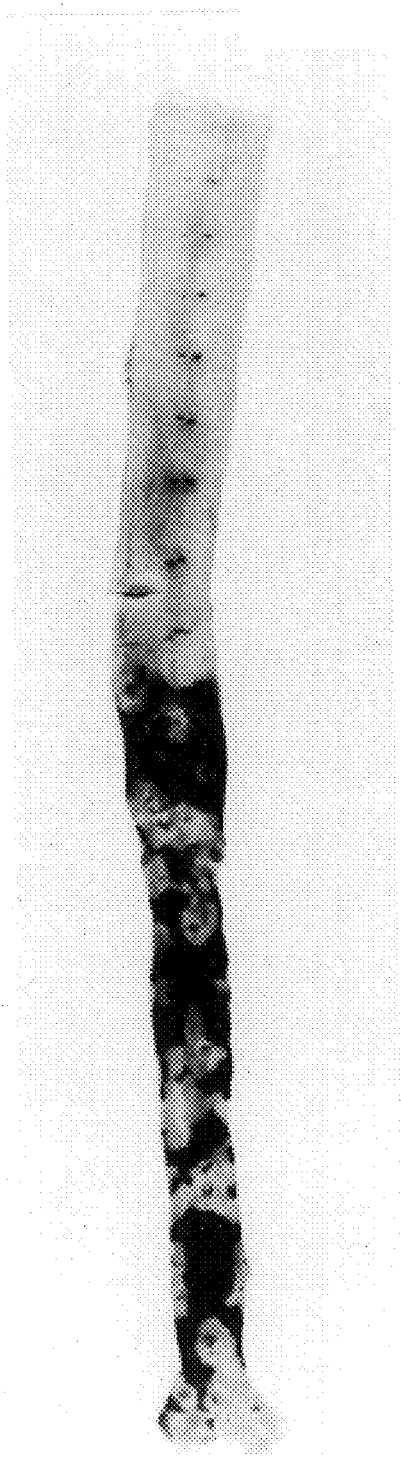
Figure 10B:
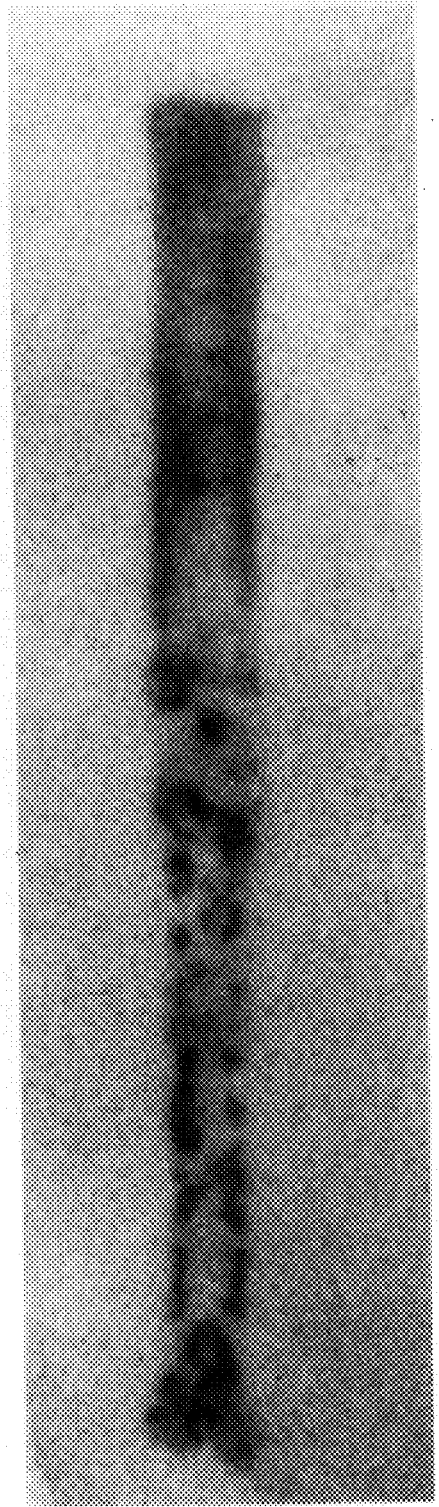
Figure 11A:
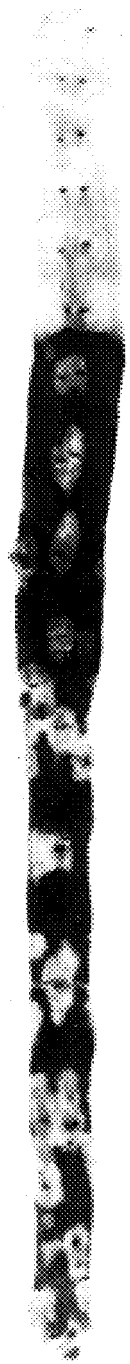
FIG. 11 shows a photograph (A) and an onlay autoradiograph (B) of the abdominal aorta of a rabbit treated with $^{125}$I-labelled synthetic peptide, SP-28.
Figure 11B:
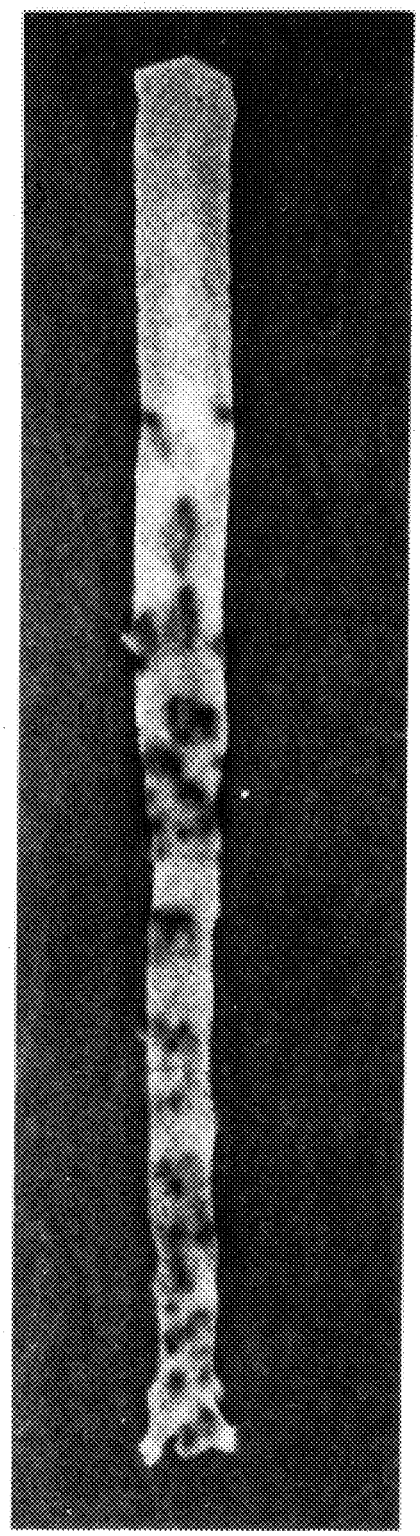
Figure 12A:
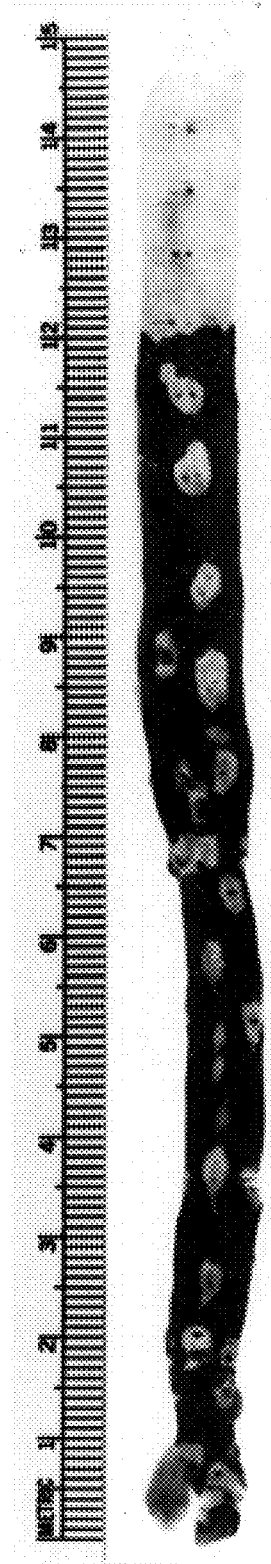
FIG. 12 shows a photograph (A) and an onlay autoradiograph (B) of the abdominal aorta of a rabbit treated with $^{125}$I-labelled synthetic peptide, SP-29.
Figure 12B:
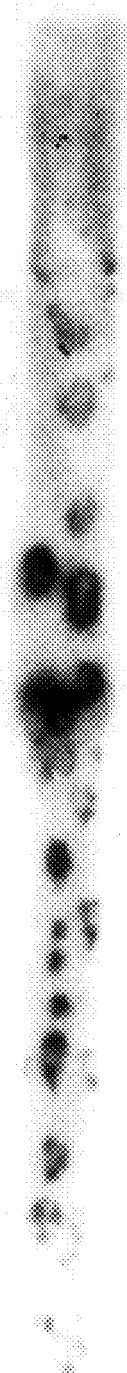
Figures 13A, 13B:
FIG. 13 shows a photograph (A) and an onlay autoradiograph (B) of the abdominal aorta of a rabbit treated with $^{125}$I-labelled synthetic peptide, SP-30.

Examples of such autoradiographs are shown in FIGS. 6 and 7 in which the $^{125}$I-labelled synthetic peptide, SP-4 was used to image arterial injury. FIG. 6 shows an onlay autoradiograph of a balloon de-endothelialized rabbit showing the labelled, healing lesions in the test portion of the aorta (B) as compared with the unlabelled control portion (A). This autoradiograph demonstrates clear-cut localization of the synthetic peptide on the image at the healing (re-endothelizing) edge of the aortic lesions produced by the previous trauma. Since this lesion is known to resemble human arteriosclerosis in many important respects, including accumulation of lipoproteins and other pathological changes, the ability of the synthetic peptides to localize at the trauma site, and to permit the imaging thereof demonstrates the utility of the present invention in imaging vascular disease. FIG. 7A shows a photograph of stained, naturally occurring lesions in the aorta of a WHHL rabbit, which clearly correspond to the radioactively-labelled lesions shown in the autoradiograph in FIG. 7B.

Similar results were obtained for peptides SP-15a, SP-17, SP-19a, SP-21a, SP-34a, SP-28, and SP-30. Representative results are shown in FIGS. 8–13. De-endothelialized arterial wall is stained blue (with Evans blue dye, as described above) and appears as dark areas in the photographs; accumulation of radiolabel is indicated by dark areas in the autoradiographs. All peptides accumulated focally at the leading edges of regenerating endothelial tissue in a pattern characteristic of LDL.

These results and others are summarized in TABLE 3 and TABLE 4. Control peptides used were SP-2 (part of the heparin and LDL receptor binding site of apolipoprotein E) and SP-11A which is a receptor and heparin binding domain of apolipoprotein B. To compare the relative accumulation of the $^{125}$I-labelled synthetic peptides in the aorta and adrenal gland, it was necessary to correct for differences in mean plasma concentration of the labelled compounds. The mean concentration of synthetic peptide-associated $^{125}$I radioactivity was calculated by numerical integration of the plasma decay curves and division by the time since injection of the isotope.

TABLE 3

| Rabbit ID | Compound Tested | Dose (μCi) | Isotope | Cir. T. (hrs) | Focal Acc'm. |
|---|---|---|---|---|---|
| B3 | sp4* | 410 | $^{125}$I | 8 | + |
| B85 | sp4* | 809 | $^{125}$I | 4.5 | + |
| B100 | sp4* | 702 | $^{125}$I | 5.5 | + |
| B87 | sp4* | 443 | $^{125}$I | (died 10 min. p injection) | |
| B156 | sp4* | 300.3 | $^{125}$I | 6 | + |
| B4 | sp4* + MV* | 80 | $^{125}$I | 24 | + |
| B39 | sp4* + MV° | 456 | $^{125}$I | 24 | + |
| B38 | sp4* + MV° | 516 | $^{125}$I | 24 | + |
| B44 | sp4* + MV° | 1000 | $^{125}$I | 24 | + |
| B56 | sp4* + MV° | 386 | $^{125}$I | 24 | + |
| B69 | sp4* + MV° | 518 | $^{125}$I | 1 | + |
| B80 | sp4* + MV° | 741 | $^{125}$I | 24 | + |
| B79 | sp4* + MV° | 664 | $^{125}$I | 4 | + |
| B25 | sp4* + MV° | 409 | $^{125}$I | 24 | + |
| B152 | sp4* + MV° | 421.2 | $^{125}$I | 6 | + |
| B24 | MV* | | $^{14}$C/$^3$H | 24 | − |
| B17 | MV* | | $^{14}$C/$^3$H | 24 | − |
| B16 | MV* | | $^{14}$C/$^3$H | 24 | − |
| B90 | sp4A* | 615 | $^{125}$I | 4 | + |
| B106 | sp4A* | 377 | $^{125}$I | 5 | + |
| B94 | sp4A* + MV° | 625 | $^{125}$I | 5 | + |
| B108 | sp4A* + MV° | 382 | $^{125}$I | 4 | + |
| B59 | sp6A* + MV° | 312 | $^{125}$I | 24 | + |
| B127 | sp6A* | 350 | $^{125}$I | 4 | + |
| B122 | sp6A* | 348 | $^{125}$I | 4 | + |
| B139 | sp6A* | 552 | $^{125}$I | 4 | + |
| B146 | sp6A* | 550.4 | $^{125}$I | 5 | + |
| IL-4 | sp6A* | 282 | $^{125}$I | 5 | + |
| IL-1 | sp6A* | 308 | $^{125}$I | 5 | + |
| B55 | sp6* | 529 | $^{125}$I | 24 | + |
| B115 | sp6* | 418 | $^{125}$I | 4 | + |
| B115-1 | sp6* | 398.9 | $^{125}$I | 4 | + |
| B111 | sp8* + MV° | 419 | $^{125}$I | 4 | + |
| B103 | sp8* | 424 | $^{125}$I | 5 | + |
| B124 | sp8* | 466.2 | $^{125}$I | 4 | + |
| B124-1 | sp8* | 445.8 | $^{125}$I | 4 | + |
| B120 | sp8A* | 315.3 | $^{125}$I | 4 | + |
| B120-1 | sp8A* | 364.5 | $^{125}$I | 5 | + |
| B137 | sp8A* | 402.6 | $^{125}$I | 4 | + |
| B135 | sp8A* | 427.7 | $^{125}$I | 5 | + |
| C-14 | sp12A* | 132.5 | $^{125}$I | 4 | + |
| C-13 | sp12A* | 110 | $^{125}$I | 4 | + |
| B590 | sp11 | 648.1 | $^{125}$I | 4 | − |
| B690 | sp11 | 363.0 | $^{125}$I | 4 | − |
| NZW-1 | sp12A* | 260.0 | $^{125}$I | 5 | + |
| NZW-2 | sp12A* | 166.4 | $^{125}$I | 4 | + |
| NZW-3 | sp14A* | 941.0 | $^{125}$I | 4 | + |
| WHHL-1 | sp2* | 318.9 | $^{125}$I | 1 | − |
| WHHL-2 | sp4* | 427.5 | $^{125}$I | 1 | + |
| WHHL-3 | sp4* | 487.8 | $^{125}$I | 4 | + |
| WHHL-4 | sp4* | 483.5 | $^{125}$I | 4 | + |
| WHHL-5 | sp4* | 688.0 | $^{125}$I | 4 | + |
| WHHL-6 | sp11* | 126.3 | $^{125}$I | 4 | − |
| WHHL-7 | sp11* | 117.1 | $^{125}$I | 4 | − |

MV = cholesterol ester microvesicles
*= radioactive
°= cold

TABLE 4

| Compound[a] Tested | Isotope | Cir. T. (hours) | Focal Acc'm |
|---|---|---|---|
| SP-34a | $^{125}$I | 4 | + |
| SP-28 | $^{125}$I | 4 | + |
| SP-30 | $^{125}$I | 4 | + |

[a]All peptides have plasma half-lives of approximately one minute. Radiolabelled peptides were injected intravenously at a dose of between 0.2–1.0 mCi.

We claim:

1. A method for detection of injury in a vascular system of a subject, comprising the steps of:
   (a) introducing into said subject an amount sufficient for later detection of a synthetic peptide having an affinity for, and a propensity to accumulate at, a site of vascular injury, wherein said peptide is water soluble, contains thirty or fewer amino acids, contains an amphiphilic domain, and bears a detectable label;
   (b) allowing said peptide to circulate within said vascular system, for a time sufficient to allow at least a portion of said peptide to accumulate at said site; and
   (c) detecting the accumulated peptide in the vascular system.

2. The method of claim 1, wherein said arterial injury in the vascular system comprises atherosclerosis.

3. The method of claim 1, wherein said peptide has a molecular conformation analogous to the molecular conformation of a surface region of the apolipoprotein B moiety of low density lipoprotein, whereby said peptide or peptide analog accumulates at said site of vascular injury.

4. The method of claim 1, wherein said peptide has a net charge of −2 or greater.

5. The method of claim 4, wherein said amphiphilic domain further comprises an α-helix.

6. The method of claim 4, wherein said peptide is derived from a vascular-associated protein.

7. The method of claim 6, wherein said vascular-associated protein is the apolipoprotein B (apoB) protein.

8. The method of claim 1, wherein said introducing step (a) comprises introducing into said subject a peptide having an acetylated amino terminus.

9. The method of claim 1, wherein said introducing step comprises introducing into said subject a peptide having an aminated carboxy terminus.

10. The method of claim 1, wherein said introducing step (a) comprises administering a peptide or peptide analog having a detectable label linked thereto.

11. The method of claim 10, wherein said detectable label is a radioactive label.

12. The method of claim 11, wherein said radioactive label is selected from the group consisting of $^{131}$I, $^{125}$I, $^{123}$I, $^{111}$In, 99m Tc, $^{203}$Pb, $^{198}$Hg, $^{97}$Ru, and $^{201}$Tl.

13. The method of claim 1, wherein said introducing step (a) comprises the administration of said peptide by arterial injection.

14. The method of claim 1, wherein said introducing step (a) comprises the administration of said peptide by venous injection.

15. The method of claim 1, wherein said introducing step (a) comprises the oral administration of said peptide.

16. The method of claim 1, wherein said introducing step (a) comprises the nasal administration of said peptide.

17. The method of claim 1, wherein said detecting step (c) further comprises imaging a region of said vascular system at which said peptide has accumulated.

18. The method of claim 1, further comprising the step of quantitating a detected amount of said labelled peptide.

19. The method of claim 1, wherein said detecting step (c) further includes the extracorporeal monitoring of said labelled peptide.

20. The method of claim 11, wherein said detecting step (c) comprises the extracorporeal monitoring of said radioactive label with a gamma scintillation camera.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 18
       (B) TYPE: amino acid
       (C) STRANDEDNESS:
       (D) TOPOLOGY:linear (xi) SEQUENCE DESCRIPTION: SEQUENCE ID NO:1:

Tyr Arg Ala Leu Val Asp Thr Leu Lys Phe Val Thr Gln Ala Glu Gly
5                   10                  15

Ala Lys (2) INFORMATION FOR SEQ ID NO:2:

(i) SEQUENCE CHARACTERISTICS:
       (A) LENGTH: 18
       (B) TYPE: amino acid
       (C) STRANDEDNESS:
       (D) TOPOLOGY:linear (xi) SEQUENCE DESCRIPTION: SEQUENCE ID NO:2:

Tyr Lys Leu Ala Leu Glu Ala Ala Arg Leu Leu Ala Asp Ala Glu Gly
            5                   10                  15

Ala Lys (2) INFORMATION FOR SEQ ID NO:3:

(i) SEQUENCE CHARACTERISTICS:
       (A) LENGTH: 18
       (B) TYPE: amino acid
       (C) STRANDEDNESS:
       (D) TOPOLOGY: linear (xi) SEQUENCE DESCRIPTION: SEQUENCE ID NO:3:

Tyr Lys Leu Ala Leu Glu Ala Ala Arg Leu Leu Ala Asn Ala Glu Gly
            5                   10                  15

Ala Lys (2) INFORMATION FOR SEQ ID NO:4:

(i) SEQUENCE CHARACTERISTICS:
       (A) LENGTH: 14
       (B) TYPE: amino acid
       (C) STRANDEDNESS:
       (D) TOPOLOGY: linear (xi) SEQUENCE DESCRIPTION: SEQUENCE ID NO:4:

Tyr Arg Ala Leu Val Asp Tyr Leu Lys Phe Val Thr Gln Leu
                5                   10

(2) INFORMATION FOR SEQ ID NO:5:

(i) SEQUENCE CHARACTERISTICS:
       (A) LENGTH: 9
       (B) TYPE: amino acid
       (C) STRANDEDNESS:
       (D) TOPOLOGY: linear (xi) SEQUENCE DESCRIPTION: SEQUENCE ID NO:5:

```
Tyr Arg Ala Leu Val Asp Thr Leu Lys
            5
```

(2) INFORMATION FOR SEQ ID NO:6:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQUENCE ID NO:6:

```
Tyr Ala Lys Phe Arg Glu Thr Leu Glu Asp Thr Arg Asp Arg Met Tyr
            5                   10                  15
```

(2) INFORMATION FOR SEQ ID NO:7:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQUENCE ID NO:7:

```
Tyr Ala Ala Leu Asp Leu Asn Ala Val Ala Asn Lys Ile Ala Asp Phe
            5                   10                  15

Glu Leu
```

(2) INFORMATION FOR SEQ ID NO:8:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQUENCE ID NO:8:

```
Tyr Arg Ala Leu Val Asp Thr Leu Lys Phe Val Thr Glu Gln Ala Lys
            5                   10                  15

Gly Ala
```

(2) INFORMATION FOR SEQ ID NO:9:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQUENCE ID NO:9:

```
Tyr Arg Ala Leu Val Asp Thr Glu Phe Lys Val Lys Gln Glu Ala Gly
            5                   10                  15

Ala Lys
```

(2) INFORMATION FOR SEQ ID NO:10:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQUENCE ID NO:10:

```
Tyr Val Leu Asp Glu Phe Arg Glu Lys Leu Asn Glu Glu Leu Glu Ala
            5                   10                  15

Leu Lys Gln Lys
```

20

(2) INFORMATION FOR SEQ ID NO:11:

(i) SEQUENCE CHARACTERISTICS:
        (A) LENGTH: 7
        (B) TYPE: amino acid
        (C) STRANDEDNESS:
        (D) TOPOLOGY: linear (xi) SEQUENCE DESCRIPTION: SEQUENCE ID NO:11:

Tyr Val Gly Val Ala Pro Gly
            5

(2) INFORMATION FOR SEQ ID NO:12:

(i) SEQUENCE CHARACTERISTICS:
        (A) LENGTH: 6
        (B) TYPE: amino acid
        (C) STRANDEDNESS:
        (D) TOPOLOGY: linear (xi) SEQUENCE DESCRIPTION: SEQUENCE ID NO:12:

Tyr Val Pro Gly Val Gly
            5

(2) INFORMATION FOR SEQ ID NO:13:

(i) SEQUENCE CHARACTERISTICS:
        (A) LENGTH: 21
        (B) TYPE: amino acid
        (C) STRANDEDNESS:
        (D) TOPOLOGY: linear (xi) SEQUENCE DESCRIPTION: SEQUENCE ID NO:13:

Tyr Val Pro Gly Val Gly Val Pro Gly Val Gly Val Pro Gly Val Gly
            5                   10                  15

Val Pro Gly Val Gly
            20

(2) INFORMATION FOR SEQ ID NO:14:

(i) SEQUENCE CHARACTERISTICS:
        (A) LENGTH: 19
        (B) TYPE: amino acid
        (C) STRANDEDNESS:
        (D) TOPOLOGY: linear (xi) SEQUENCE DESCRIPTION: SEQUENCE ID NO:14:

Tyr Val Gly Val Ala Pro Gly Val Gly Val Ala Pro Gly Val Gly Val
            5                   10                  15

Ala Pro Gly (2) INFORMATION FOR SEQ ID NO:15:

(i) SEQUENCE CHARACTERISTICS:
        (A) LENGTH: 5
        (B) TYPE: amino acid
        (C) STRANDEDNESS:
        (D) TOPOLOGY: linear (xi) SEQUENCE DESCRIPTION: SEQUENCE ID NO:15:

Val Pro Gly Val Gly
            5

(2) INFORMATION FOR SEQ ID NO:16:

(i) SEQUENCE CHARACTERISTICS:
    (A) LENGTH: 6
    (B) TYPE: amino acid
    (C) STRANDEDNESS:
    (D) TOPOLOGY: linear (xi) SEQUENCE DESCRIPTION: SEQUENCE ID NO:16:

Val Gly Val Ala Pro Gly
            5

(2) INFORMATION FOR SEQ ID NO:17:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQUENCE ID NO:17:

Tyr Val Pro Gly Val Gly Val Pro Gly Val Gly Val Pro Gly Val Gly
             5                  10                  15

(2) INFORMATION FOR SEQ ID NO:18:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQUENCE ID NO:18:

Lys Phe Val Thr Gln Ala Glu Gly Ala Lys
             5                  10

(2) INFORMATION FOR SEQ ID NO:19:

(i) SEQUENCE CHARACTERISTICS:
        (A) LENGTH: 17
        (B) TYPE: amino acid
        (C) STRANDEDNESS:
        (D) TOPOLOGY: linear (xi) SEQUENCE DESCRIPTION: SEQUENCE ID NO:19:

Lys Leu Pro Gln Gln Ala Asn Asp Tyr Leu Asn Ser Phe Asn Glu
             5                  10                  15

Arg (2) INFORMATION FOR SEQ ID NO:20:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQUENCE ID NO:20:

Leu Pro Gln Gln Ala Asn Asp Tyr
             5

(2) INFORMATION FOR SEQ ID NO:21:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQUENCE ID NO:21:

-continued

Lys Phe Arg Glu Thr Leu Glu Asp Thr Arg
                5                  10

(2) INFORMATION FOR SEQ ID NO:22:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQUENCE ID NO:22:

Arg Ile Ser Leu Pro Asp Phe Arg
                5

(2) INFORMATION FOR SEQ ID NO:23:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQUENCE ID NO:23:

Arg Thr Phe Gln Ile Pro Gly Tyr Thr Val Pro Val Val Asn Val Glu
                5                  10                  15

Val Ser Pro Phe
            20

(2) INFORMATION FOR SEQ ID NO:24:

(i) SEQUENCE CHARACTERISTICS:
        (A) LENGTH: 26
        (B) TYPE: amino acid
        (C) STRANDEDNESS:
        (D) TOPOLOGY: linear (xi) SEQUENCE DESCRIPTION: SEQUENCE ID NO:24:

Tyr Thr Val Pro Val Val Asn Val Glu Val Ser Pro Phe Thr Ile Glu
                5                  10                  15

Met Ser Ala Phe Gly Tyr Val Phe Pro Lys
            20                  25

(2) INFORMATION FOR SEQ ID NO:25:

(i) SEQUENCE CHARACTERISTICS:
        (A) LENGTH: 21
        (B) TYPE: amino acid
        (C) STRANDEDNESS:
        (D) TOPOLOGY: linear (xi) SEQUENCE DESCRIPTION: SEQUENCE ID NO:25:

Arg Val Pro Ser Tyr Thr Leu Ile Leu Pro Ser Leu Glu Leu Pro Val
                5                  10                  15

Leu His Val Pro Arg
            20

(2) INFORMATION FOR SEQ ID NO:26:

(i) SEQUENCE CHARACTERISTICS:
        (A) LENGTH: 22
        (B) TYPE: amino acid
        (C) STRANDEDNESS:
        (D) TOPOLOGY: linear (xi) SEQUENCE DESCRIPTION: SEQUENCE ID NO:26:

Lys Ile Ala Asp Phe Glu Leu Pro Thr Ile Ile Val Pro Glu Gln Thr

```
                         5              10              15
Ile Glu Ile Pro Ser Ile
                     20

(2) INFORMATION FOR SEQ ID NO:27:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQUENCE ID NO:27:

Arg Asn Leu Gln Asn Asn Ala Glu Trp Val Tyr Gln Gly Ala Ile Arg
                 5                  10                  15
```